(12) United States Patent
Zhang et al.

(10) Patent No.: US 11,623,926 B2
(45) Date of Patent: Apr. 11, 2023

(54) COMPOUND, OLED DISPLAY PANEL AND ELECTRONIC DEVICE

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Lei Zhang, Shanghai (CN); Wei Gao, Shanghai (CN); Jinghua Niu, Shanghai (CN); Wenpeng Dai, Shanghai (CN); Yan Lu, Shanghai (CN); Yang Li, Shanghai (CN); Ying Liu, Shanghai (CN)

(73) Assignee: WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 469 days.

(21) Appl. No.: 16/731,757

(22) Filed: Dec. 31, 2019

(65) Prior Publication Data

US 2020/0140416 A1   May 7, 2020

(30) Foreign Application Priority Data

Jun. 27, 2019   (CN) .......................... 201910569617.8

(51) Int. Cl.
*C07D 403/14*   (2006.01)
*C07D 401/14*   (2006.01)
(Continued)

(52) U.S. Cl.
CPC ......... *C07D 403/14* (2013.01); *C07D 401/14* (2013.01); *H01L 51/0067* (2013.01); *H01L 51/0072* (2013.01); *H01L 51/5092* (2013.01)

(58) Field of Classification Search
CPC ............. C07D 403/14; H01L 51/0067; H01L 51/0072
See application file for complete search history.

(56) References Cited

U.S. PATENT DOCUMENTS

| 7,777,043 B2* | 8/2010 | Yabe | H01L 51/0067 546/255 |
| 2012/0126692 A1* | 5/2012 | Ise | H05B 33/14 252/301.16 |

(Continued)

FOREIGN PATENT DOCUMENTS

| CN | 1753967 A | 3/2006 |
| CN | 108290900 A | 7/2018 |

(Continued)

OTHER PUBLICATIONS

Computer-generated English-language translation of KR-20180020577-A.*

(Continued)

*Primary Examiner* — Vu A Nguyen
(74) *Attorney, Agent, or Firm* — Alston & Bird LLP

(57) ABSTRACT

The present disclosure describes an electroluminescent material which is formed of a compound having a structure of Formula (I), an OLED display panel utilizing the compound and an electronic device having the OLED display panel. The OLED display panel includes a first electrode, a second electrode, and an organic thin film layer disposed between the first electrode and the second electrode. The organic thin film layer comprises an electron transport layer which comprises any one or a combination of at least two of the compounds. The electroluminescent material has a triplet energy level $E_T$ of ≥2.7 eV, a HOMO energy level of ≤−5.85 eV, and a glass transition temperature of >120° C.

(Continued)

This compound improves luminous efficiency in the OLED display panel and the electronic device.

11 Claims, 2 Drawing Sheets

(51) Int. Cl.
  *H01L 51/00* (2006.01)
  *H01L 51/50* (2006.01)

(56) References Cited

U.S. PATENT DOCUMENTS

| | | |
|---|---|---|
| 2013/0313531 A1 | 11/2013 | Kaminaga et al. |
| 2016/0329502 A1 | 11/2016 | Dyatkin et al. |
| 2017/0186962 A1* | 6/2017 | Ren .................... H01L 51/0054 |

FOREIGN PATENT DOCUMENTS

| | | | | |
|---|---|---|---|---|
| JP | 2012062450 A | | 3/2012 | |
| KR | 20100131939 A | | 12/2010 | |
| KR | 20110105285 A | * | 9/2011 | ............. C09K 11/06 |
| KR | 20110105285 A | | 9/2011 | |
| KR | 20180020577 A | * | 2/2018 | ........... C07D 401/14 |
| WO | WO-2011071255 A1 | * | 6/2011 | ........... C07D 401/14 |

OTHER PUBLICATIONS

Computer-generated English-language translation of KR-20110105285-A.*

\* cited by examiner

COMPOUND, OLED DISPLAY PANEL AND ELECTRONIC DEVICE

CROSS-REFERENCE TO RELATED APPLICATIONS

The application claims the benefit of the earlier filing date of Chinese Patent Application No. CN201910569617.8, filed on Jun. 27, 2019 to the China National Intellectual Property Administration, the contents of which are incorporated by reference herein in its entirety.

TECHNICAL FIELD

The present disclosure relates to the technical field of OLED display panels, and in particular, to a compound, an OLED display panel and an electronic device.

BACKGROUND

With the commercialization and application of electroluminescent devices, electron transport materials with higher transport efficiency and better performance are desired and some exploratory work has been done in this field by researchers. The electron transport material used in conventional electroluminescent devices is tris (8-hydroxyquinoline) aluminum (Alq3) which has a relative low electron mobility (about $10^{-6}$ cm$^2$/Vs) such that the electron transport of and the hole transport of the device is not balanced. With the commercialization and application of electroluminescent devices, ETL materials with higher transport efficiency and better performance are desired and a lot of exploratory work has been done in this field by researchers.

Although current electron transport materials widely used on the market, such as batho-phenanthroline (BPhen), bathocuproine (BCP) and TmPyPB generally meet the market demand for organic electroluminescent panels, they have a relative low glass transition temperature which is generally less than 85° C. As a result, the Joule heat generated by a device in operation will lead to molecular degradation and molecular structure changes, which make the panel have low efficiency and poor thermal stability. Moreover, such molecular has an extremely regular symmetrical structure such that crystallization is easily occurred after a long-term use. Once the electron transport material crystallizes, the mechanism of charge transition between molecules will be different from that in an amorphous film in normal operation, resulting in a decrease in electron transport performance, unbalanced electron and hole mobility of the entire device, a great decrease in the efficiency of exciton formation, and that exciton formation is mainly occurred at the interface between the electron transport layer and the light-emitting layer, resulting in a serious decrease in device efficiency and lifetime.

Therefore, it is necessary to develop an electron transport material having a high triplet energy level, high electron mobility, and excellent thermal stability and film stability.

SUMMARY

In a first aspect, the present disclosure provides a compound, which has the structure of Formula (I):

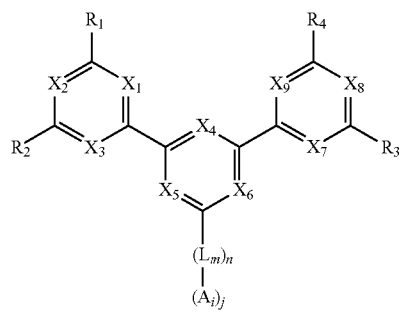

Formula (I)

In Formula (I), $R_1$, $R_2$, $R_3$ and $R_4$ each is independently any one selected from a group consisting of a substituted or unsubstituted C6-C40 aromatic ring and a substituted or unsubstituted C5-C40 heteroaromatic ring.

Also in Formula (I), $X_1$, $X_2$, $X_3$, $X_4$, $X_5$, $X_6$, $X_7$, $X_8$ and $X_9$ each is independently selected from a carbon atom or a nitrogen atom, and at least one of $X_1$, $X_2$, $X_3$, $X_4$, $X_5$, $X_6$, $X_7$, $X_8$ and $X_9$ is a nitrogen atom. $L_m$ is each independently any one selected from a group consisting of a substituted or unsubstituted C6-C40 arylene and a substituted or unsubstituted C5-C40 heteroarylene. n is selected from 0 or 1, and m is 1; $A_i$ is each independently any one selected from a group consisting of a substituted or unsubstituted carbazolyl and a derivative group thereof, a substituted or unsubstituted bicarbazolyl and a derivative group thereof, a substituted or unsubstituted arylamino and a derivative group thereof, a substituted or unsubstituted acridinyl and a derivative group thereof, a substituted or unsubstituted phenothiazinyl and a derivative group thereof, a substituted or unsubstituted phenoxazinyl and a derivative group thereof, and a substituted or unsubstituted phenazinyl and a derivative group thereof; j is an integer from 1 to 3, and i is an integer from 1 to j;

A substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group.

In a second aspect, the present disclosure provides an OLED display panel, which comprises a first electrode, a second electrode, and an organic thin film layer disposed between the first electrode and the second electrode; wherein the organic thin film layer comprises an electron transport layer; wherein the material of the electron transport layer comprises any one or a combination of at least two of the compounds as described in the first aspect.

In a third aspect, the present disclosure provides an electronic device, which comprises the OLED display panel as described in the second aspect.

DETAILED DESCRIPTION

Figure 1:
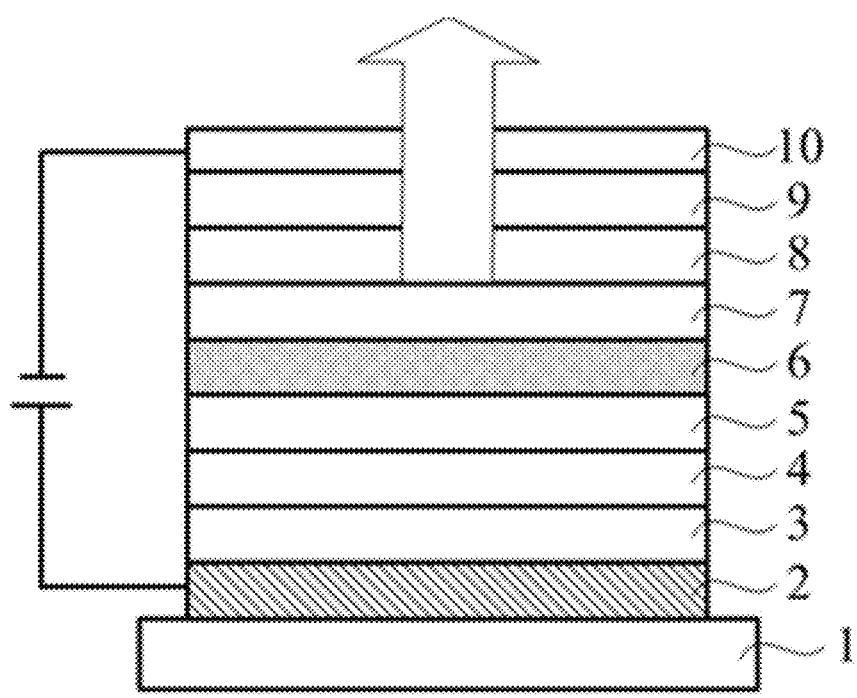
FIG. 1 shows a schematic view of an OLED display panel, in accordance of an embodiment of the present disclosure.

For the purpose of understanding the present disclosure, the following examples are listed below in the present disclosure. It will be apparent to those skilled in the art that the examples are merely illustrations of the present disclosure and should not be construed as specific limitations to the present disclosure.

One embodiment provides a compound, which has the structure of Formula (I):

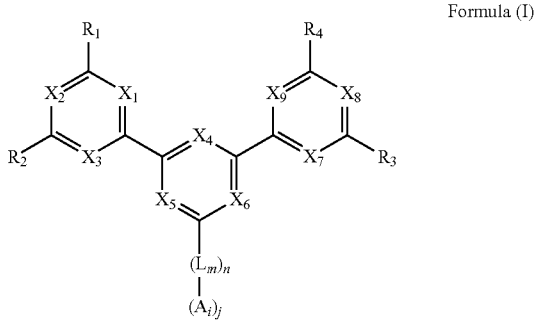

Formula (I)

In Formula (I), $R_1$, $R_2$, $R_3$, $R_4$ each is independently any one selected from a group consisting of a substituted or unsubstituted C6-C40 aromatic ring and a substituted or unsubstituted C5-C40 heteroaromatic ring; $X_1$, $X_2$, $X_3$, $X_4$, $X_5$, $X_6$, $X_7$, $X_8$ and $X_9$ each is independently selected from a carbon atom or a nitrogen atom, and at least one of $X_1$, $X_2$, $X_3$, $X_4$, $X_5$, $X_6$, $X_7$, $X_8$ and $X_9$ is a nitrogen atom; $L_m$ is any one independently selected from a group consisting of a substituted or unsubstituted C6-C40 arylene and a substituted or unsubstituted C5-C40 heteroarylene; n is selected from 0 or 1, and m is 1; $A_i$ is any one independently selected from a group consisting of a substituted or unsubstituted carbazolyl and a derivative group thereof, a substituted or unsubstituted arylamino and a derivative group thereof, and a substituted or unsubstituted acridinyl and a derivative group thereof; j is an integer from 1 to 3, such as 1, 2 and 3, and i is an integer from 1 to j.

The substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group.

C1 to C10 may be C1, C2, C3, C4, C5, C6, C7, C8, C9, and C10. C2 to C10 may be C2, C3, C4, C5, C6, C7, C8, C9, and C10. C1 to C6 may be C1, C2, C3, C4, C5, and C6. C6 to C30 may be C6, C8, C10, C12, C14, C16, C18, C20, C22, C24, C26, C28, and C30. C3 to C30 may be C3, C4, C6, C8, C10, C12, C14, C16, C18, C20, C22, C24, C26, C28, and C30.

In Formula (I), $A_i$ and $L_m$ are used to represent substituents. $A_i$ and $L_m$ are intended to represent the range of choice of a group rather than a specific group. When the number of $A_i$ is greater than or equal to 2, the substituents $A_i$ may be the same or different. Illustratively, if two $A_i$ groups are on the parent group, i.e., j is 2, i is an integer selected from 1 or 2. If i in both $A_i$ is 1, two $A_1$ groups are on the parent group and these two $A_1$ groups are the same. If i in these two $A_i$ is 1 and 2, respectively, $A_1$ and $A_2$ are on the parent group and these two $A_i$ groups may be the same or different.

The compound provided by the present disclosure comprises a nitrogen-containing heteroaromatic ring as a parent ring in combination with a particular electron-donating group, so that the obtained compound has a suitable HOMO level and a low LUMO level, improving the electron transporting ability and effectively blocking holes; has high electron mobility, ensuring that electrons can recombine in the light-emitting layer so that the rate of exciton generation is increased; has a high glass transition temperature and a high thermal decomposition temperature, preventing Joule heat generated by the device in operation from affecting device lifetime and efficiency; has excellent film stability and uniformity, avoiding degradation or attenuation induced by light scattering or crystallization; and has a high reduction potential which is suitable for electron transport. The obtained compound may have a triplet energy level $E_T$ of $\geq 2.7$ eV, a HOMO energy level of $\leq -5.85$ eV, and a glass transition temperature of $>120°$ C. In addition, this structure is ambipolar so that the compound has a small excited state dipole moment and, when used as a host light-emitting material, can effectively reduce the efficiency roll-off and improve the luminescence brightness and luminescence efficiency. When used as an electron transport material for an OLED panel, the compound can effectively improve the electron mobility of the device, thereby ensuring a high luminous efficiency, a long service life, and a low threshold voltage.

In an embodiment, at least one of $X_1$, $X_2$, $X_3$, $X_7$, $X_8$ and $X_9$ is a nitrogen atom.

In the present disclosure, at least one of $X_1$, $X_2$, $X_3$, $X_7$, $X_8$ and $X_9$ is a nitrogen atom. The N atom allows the doped group to have a corresponding electron accepting ability to ensure that the LUMO energy level of the material matches the adjacent layer.

In an embodiment, two to six such as 2, 3, 4, 5 or 6 of $X_1$, $X_2$, $X_3$, $X_4$, $X_5$, $X_6$, $X_7$, $X_8$ and $X_9$ are nitrogen atoms.

In the present disclosure, two to six of $X_1$, $X_2$, $X_3$, $X_4$, $X_5$, $X_6$, $X_7$, $X_8$ and $X_9$ are nitrogen atoms, which can effectively adjust the LUMO energy level of the molecule, thereby improving the electron transporting ability of the compound and effectively blocking holes.

In an embodiment, $L_m$ is any one independently selected from a group consisting of

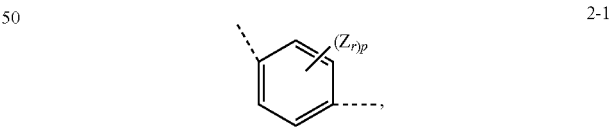

2-1

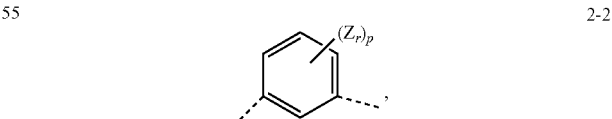

2-2

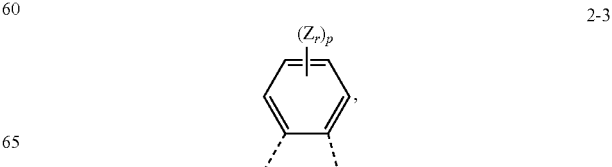

2-3

-continued 2-4 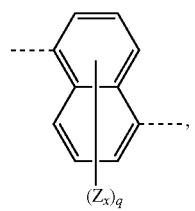

2-5 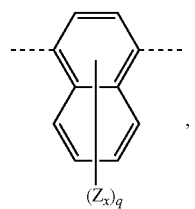

2-6 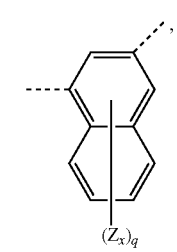

2-7 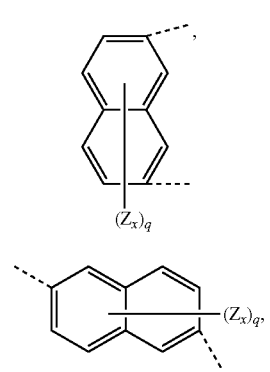

2-8 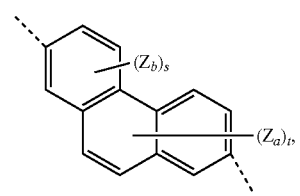

2-9 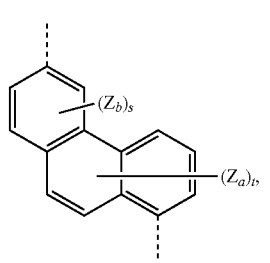

2-10 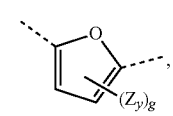

2-11

-continued 2-12 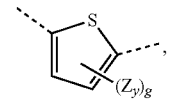

2-13 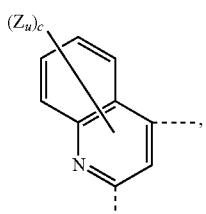

2-14 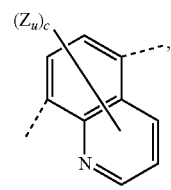

2-15 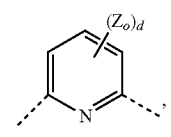

2-16 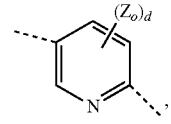

2-17 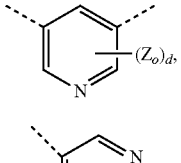

2-18 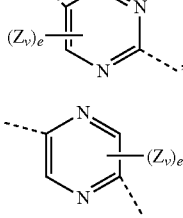

2-19 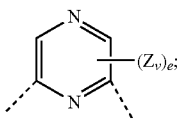

2-20 wherein $Z_r$, $Z_x$, $Z_a$, $Z_b$, $Z_y$, $Z_u$, $Z_o$ and $Z_v$ each is independently selected from a group consisting of a hydrogen atom, a substituted or unsubstituted C6-C30 aryl, a substituted or unsubstituted C6-C30 heteroaryl, a substituted or unsubstituted C6-C30 fused aryl, a substituted or unsubstituted C6-C30 fused heteroaryl, a substituted or unsubstituted C1-C16 alkylene, and a substituted or unsubstituted C1-C16 alkyleneoxy;

p is an integer from 0 to 4, and r is an integer from 1 to p;

q is an integer from 0 to 6, and x is an integer from 1 to q;

s and t each is independently selected from an integer from 0 to 3, a is an integer from 1 to t, and b is an integer from 1 to s;

g is an integer from 0 to 2, and y is an integer from 1 to g;

c is an integer from 0 to 5, and u is an integer from 1 to c;

d is an integer from 0 to 3, and o is an integer from 1 to d;

e is an integer from 0 to 2, and v is an integer from 1 to e;

a substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group;

wherein a dotted line indicates an attachment site.

In an embodiment, $L_m$ is preferably any one of the structures as described above because the structures as described above are simple, and thus can avoid the introduction of an excessively complex group which will increase the instability in a molecular electrochemical environment and affect the service life of the device, and can improve the solubility and triplet energy level of the molecular as much as possible. In addition, a compound having a large molecular weight is not readily vapor-deposited. Therefore, the structure of the compound should be designed to be as simple as possible without affecting the luminescent properties of the compound.

In an embodiment, $L_m$ is each independently any one selected from a group consisting of

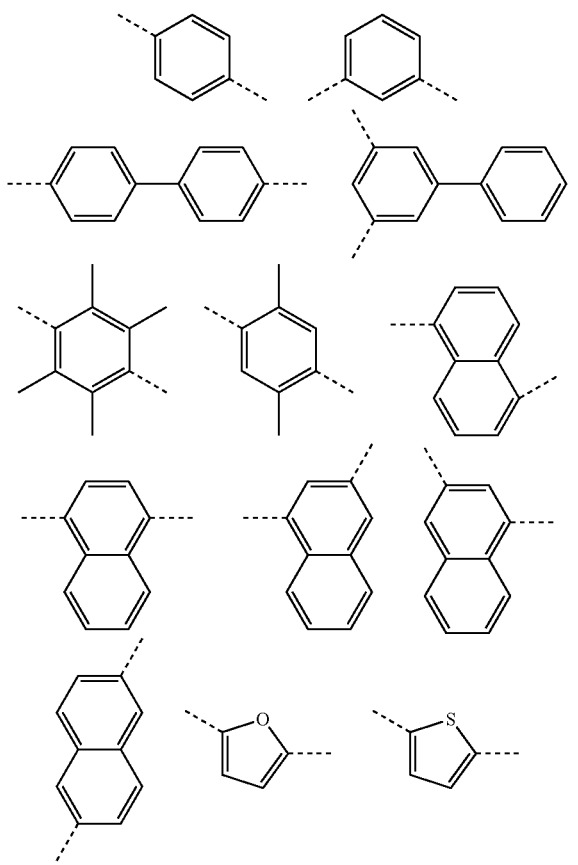

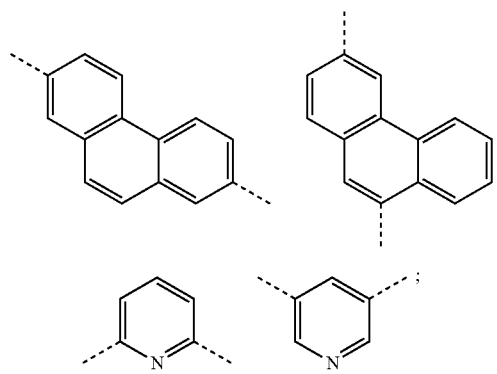

wherein a dotted line indicates an attachment site.

In an embodiment, $L_m$ is further preferably any one of the structures as described above because the structures as described above are simple. Thus, on the one hand, the introduction of an excessively complex group which will affect the service life of the device is avoided, and the solubility and triplet energy level of the molecular are improved as much as possible. On the other hand, the difficulties in vapor-depositing a compound having a large molecular weight are avoided. Therefore, the luminescence efficiency and service life of the device are improved.

In an embodiment, $A_i$ is each independently selected from a substituted or unsubstituted carbazolyl and a derivative group thereof, which are selected from a group consisting of

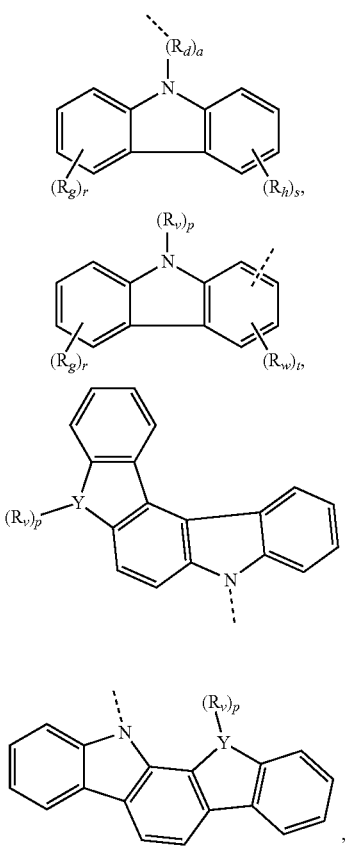

-continued

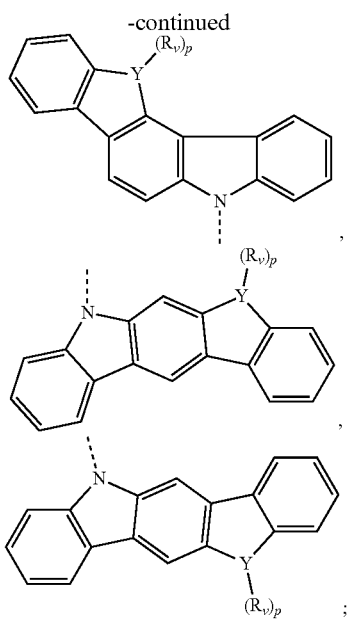

wherein Y is any one selected from a group consisting of a carbon atom, a nitrogen atom, an oxygen atom, a sulfur atom, and a silicon atom;

r and s each is independently selected from an integer from 0 to 4, g is an integer from 1 to r, and h is an integer from 1 to s, t is an integer from 0 to 3, and w is an integer from 1 to t, p is an integer from 0 to 2, and v is an integer from 1 to p, a is an integer from 0 to 5, and d is an integer from 1 to a;

$R_g$, $R_h$, $R_v$ and $R_w$ each is independently any one selected from a group consisting of a hydrogen atom, a C1-C20 alkyl, a C1-C20 alkoxy, a substituted or unsubstituted C6-C40 aryl, a substituted or unsubstituted C4-C40 heteroaryl, a substituted or unsubstituted C12-C40 carbazolyl and a derivative group thereof, a substituted or unsubstituted C12-C40 diphenylamino and a derivative group thereof, and a substituted or unsubstituted C12-C40 acridinyl and a derivative group thereof;

$R_d$ is each independently any one selected from a group consisting of a substituted or unsubstituted C1-C20 alkylene, a substituted or unsubstituted C1-C20 alkyleneoxy, a substituted or unsubstituted C6-C30 arylene, and a substituted or unsubstituted C3-C30 heteroarylene;

a substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group;

a dotted line indicates an attachment site.

In an embodiment, $A_i$ is preferably a substituted or unsubstituted carbazolyl or a derivative group thereof which has a relatively weak electron-donating group such that the HOMO level is shifted downward, which can effectively block holes from passing through the light-emitting layer, enhance the composite efficiency of holes and electrons, and broaden the light-emitting area, thereby increasing the service life of the device.

In an embodiment, the substituted or unsubstituted carbazolyl and the derivative group thereof are selected from a group consisting of

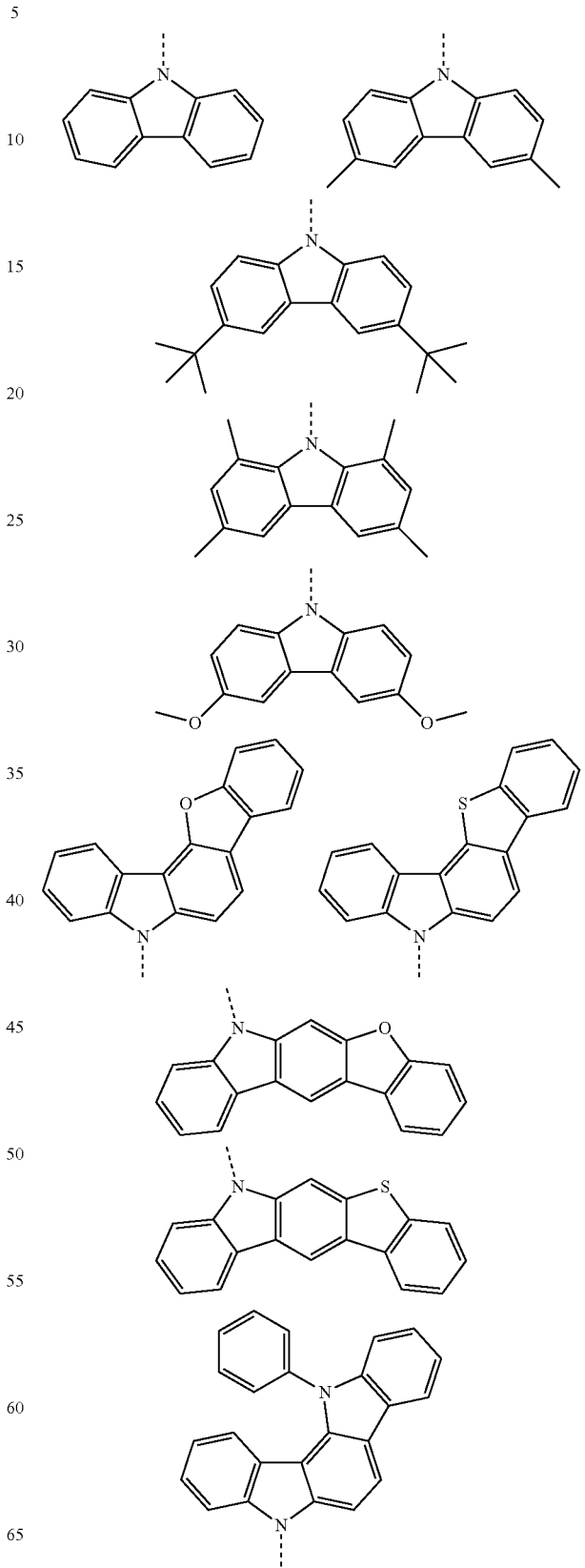

-continued

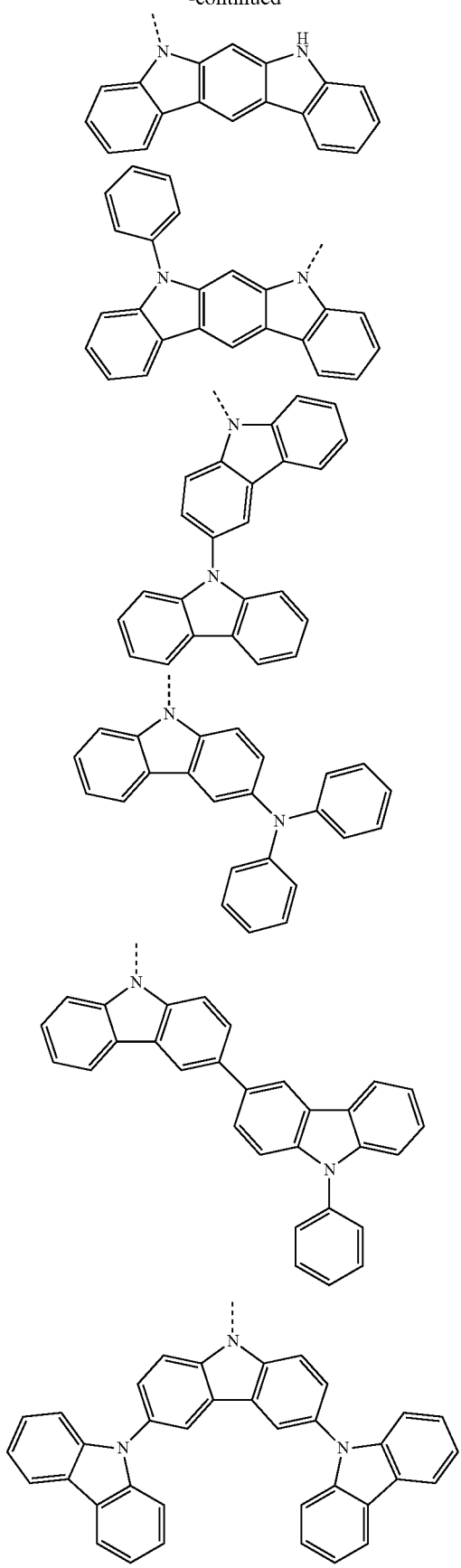

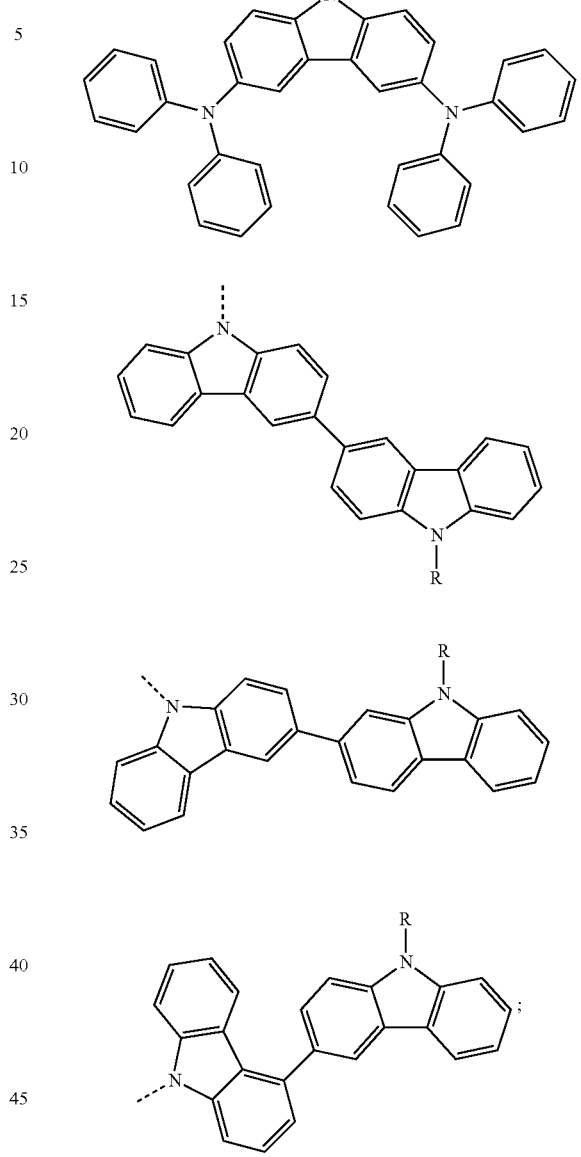

wherein R is any one selected from a group consisting of a C1-C20 alkyl, a C1-C20 alkoxy, a C2-C20 alkenyl, a C2-C20 alkynyl, a C4-C8 cycloalkyl, a C6-C40 aryl and a C4-C40 heteroaryl, here a dotted line indicates an attachment site.

In an embodiment, the substituted or unsubstituted carbazolyl and the derivative group thereof are further preferably selected from the structures as described above. In those structures, asteric hindrance between molecules is large, a twist of a molecule itself is large which increases the solubility of the molecule, and a connection with a weak electron-donating group can effectively adjust the electron donating and accepting ability of the molecule, thereby matching different material systems.

In an embodiment, $A_i$ is each independently selected from a substituted or unsubstituted acridinyl and a derivative group thereof, which are selected from a group consisting of

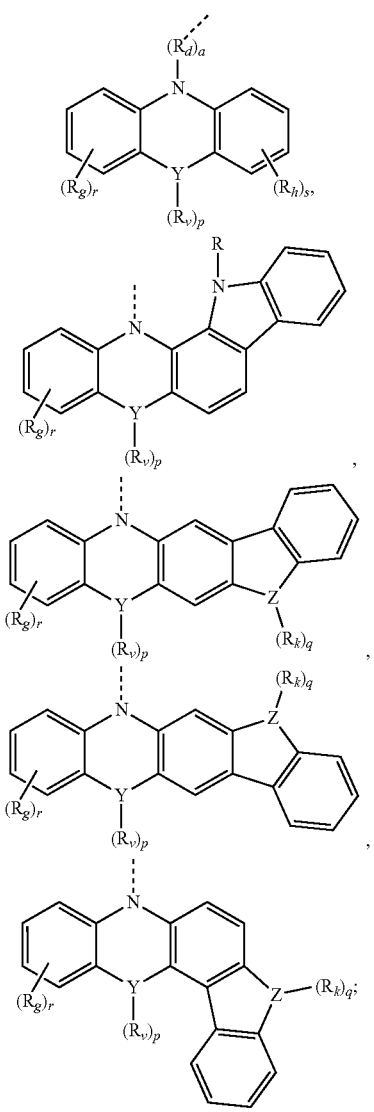

wherein Y and Z each is independently selected from a group consisting of a carbon atom, a nitrogen atom, an oxygen atom, a sulfur atom, and a silicon atom;

r and s each is independently selected from an integer from 0 to 4, g is an integer from 1 to r, and h is an integer from 1 to s, p and q each is independently selected from an integer from 0 to 2, v is an integer from 1 to p, and k is an integer from 1 to q, a is an integer from 0 to 5, and d is an integer from 1 to a;

$R_g$, $R_h$, $R_v$ and $R_k$ each is independently any one or a combination of at least two selected from a group consisting of a hydrogen atom, a C1-C20 alkyl, a C1-C20 alkoxy, a substituted or unsubstituted C6-C40 aryl, a substituted or unsubstituted C4-C40 heteroaryl, a substituted or unsubstituted C12-C40 carbazolyl and a derivative group thereof, a substituted or unsubstituted C12-C40 diphenylamino and a derivative group thereof, a substituted or unsubstituted C12-C40 acridinyl and a derivative group thereof, and a substituted or unsubstituted C3-C40 azinyl and a derivative group thereof;

$R_d$ is each independently any one selected from a group consisting of a substituted or unsubstituted C1-C20 alkylene, a substituted or unsubstituted C1-C20 alkyleneoxy, a substituted or unsubstituted C6-C30 arylene, and a substituted or unsubstituted C3-C30 heteroarylene;

the substituent is any one of a group consisting of a C1-C10 alkyl or cycloalkyl, a C2-C10 alkenyl, a C1-C6 alkoxy or a thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group;

a dotted line indicates an attachment site.

In an embodiment, $A_i$ is preferably a substituted or unsubstituted acridinyl or a derivative group thereof. Due to the strong electron donating ability of the acridinyl group, the HOMO level of the molecule is shifted upward to match a suitable parent core and thus the molecule can be used as a host material. The molecule is readily to be synthesized because a better solubility of the molecule as a result of the sp$^3$ hybridization of N atoms in the acridinyl group. When Y in the derivative group of acridinyl is N, the phenazine structure has a strong electron donating ability, while the parent ring structure of the compound has a strong electron accepting ability, such that the compound has a reduced band gap and a reduced triplet state and thus is suitable for use as a host material, preferably as a red light host material. When Y in the derivative group of acridinyl is O/S, a group has a relative low electron donating ability compared to phenazine, such that the band gap is relatively large, and the triplet state is relatively large, and thus the compound is suitable for use as a host material, preferably as a red light host material and a green light host material.

In an embodiment, the substituted or unsubstituted acridinyl and the derivative group thereof are selected from a group consisting of the following chemicals with structures of:

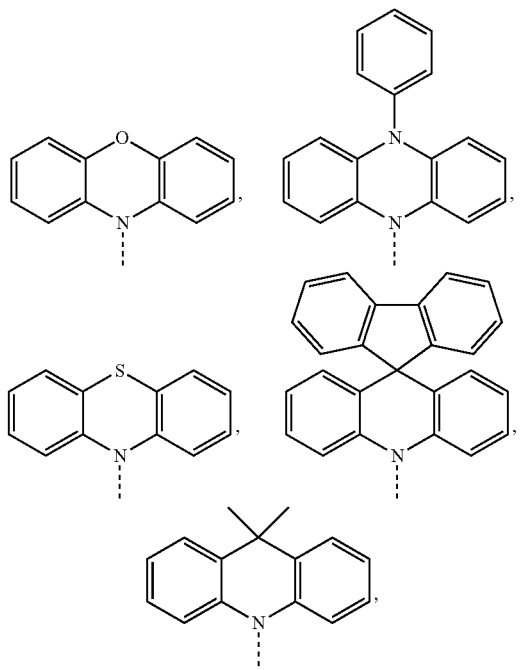

-continued

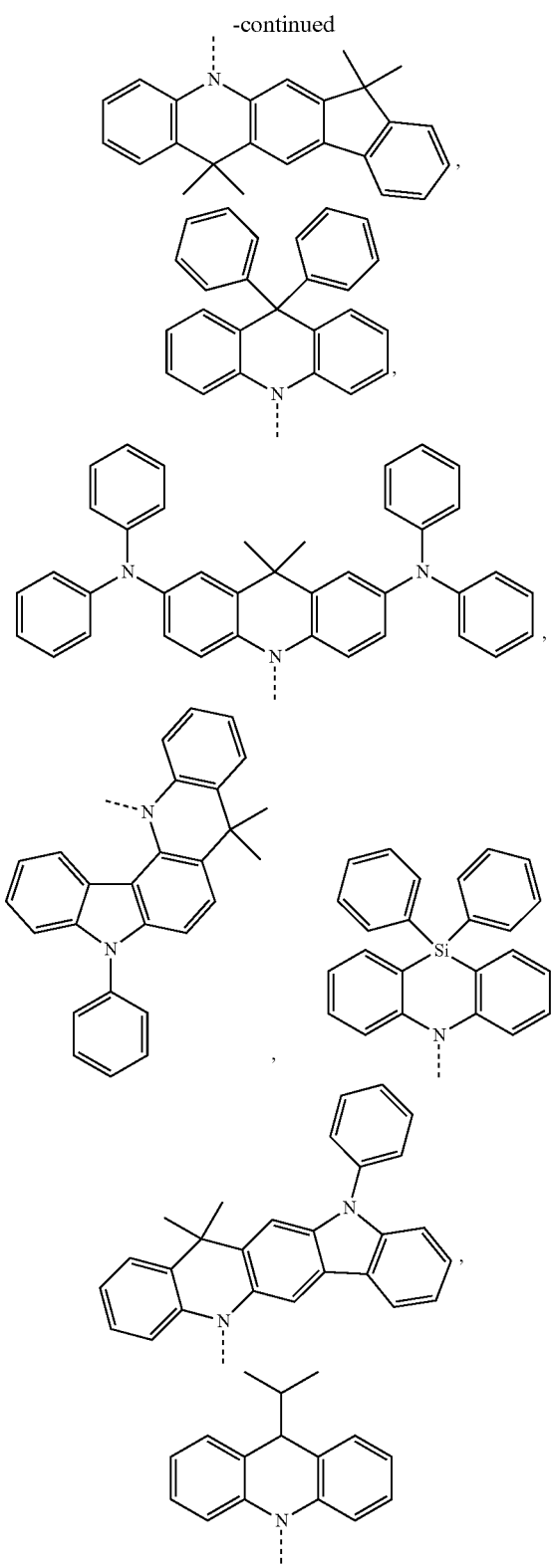

wherein a dotted line indicates an attachment site.

It is further preferred in the present disclosure that the substituted or unsubstituted acridinyl and the derivative group thereof are selected from the above structures. In such embodiment, the introduction of excessive functional groups which will increase the instability in a molecular electro- chemical environment and affect the service life of the device is avoided, and the compound may have a better solubility, thereby improving the luminous efficiency and life of the device. In addition, a compound having a large molecular weight is not readily vapor-deposited. Therefore, the structure of the compound should be designed to be as simple as possible without affecting the luminous efficiency of the compound.

In an embodiment, $A_i$ is each independently selected from a substituted or unsubstituted arylamino and a derivative group thereof, which are selected from a group consisting of the following chemical of a structure as:

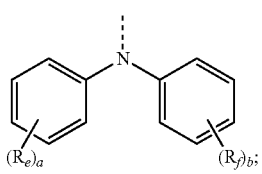

wherein both a and b are independently selected from an integer from 0 to 5, e is an integer from 1 to a, and f is an integer from 1 to b, $R_e$ and $R_f$ each is independently any one selected from a group consisting of a hydrogen atom, a C1-C20 alkyl, a C1-C20 alkoxy, a substituted or unsubstituted C6-C40 aryl, a substituted or unsubstituted C4-C40 heteroaryl, a substituted or unsubstituted C12-C40 carbazolyl and a derivative group thereof, a substituted or unsubstituted C12-C40 diphenylamino and a derivative group thereof, a substituted or unsubstituted C12-C40 acridinyl and a derivative group thereof, and a substituted or unsubstituted C3-C40 azinyl and a derivative group thereof;

a substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group;

a dotted line indicates an attachment site.

In an embodiment, $A_i$ is preferably a substituted or unsubstituted arylamine or a derivative group thereof because of reasons listed as follows: An electron donating ability of the arylamine group is between that of a carbazole derivative and that of a acridine derivative, thus the arylamine group can effectively adjust the HOMO energy level of the molecule, is suitable for different material systems and better matches adjacent layers. Moreover, the aromatic amine and its derivative group are relatively stable such that the formed molecules have good thermal stability and high triplet energy level, are suitable for use as host materials, preferably as red and green host materials, and meet the requirements of the mass production line for thermal stability.

In an embodiment, the substituted or unsubstituted arylamino and the derivative group thereof are selected from a group consisting of

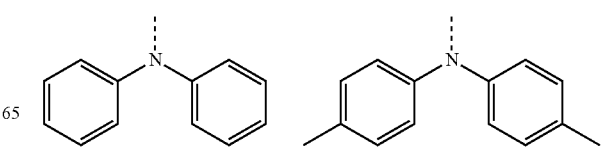

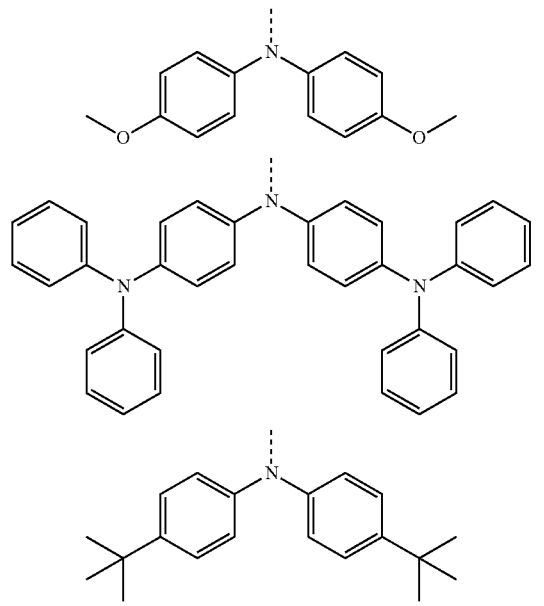

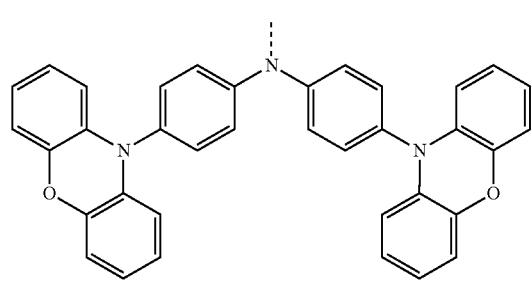

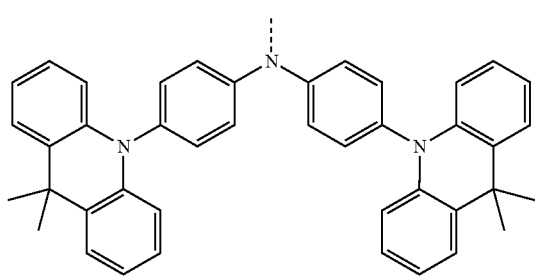

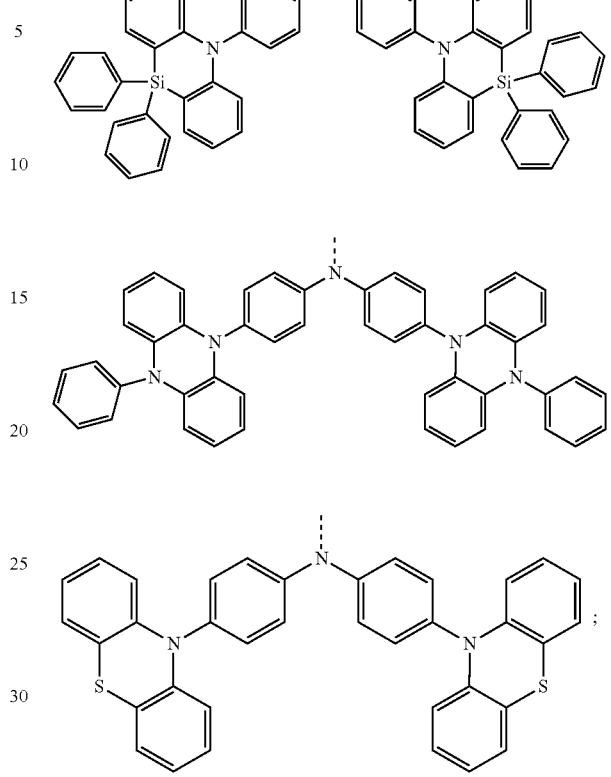

wherein a dotted line indicates an attachment site.

It is further preferred in the present disclosure that the substituted or unsubstituted arylamine and the derivative group thereof are selected from the above structures. In such embodiment, the introduction of excessive functional groups which will increase the instability in a molecular electrochemical environment and affect the service life of the device is avoided, and the compound may have a better solubility. In addition, a compound having a large molecular weight is not readily vapor-deposited. Therefore, the structure of the compound should be designed to be as simple as possible without affecting the luminous efficiency of the compound.

In an embodiment, $R_1$ and $R_4$ are the same, and $R_2$ and $R_3$ are the same.

In the present disclosure, it is preferred that $R_1$ and $R_4$ are the same, and $R_2$ and $R_3$ are the same, such that the compound has good molecular symmetry and is readily to be synthesized, and the electron accepting abilities between the electron accepting groups of the compound can be ensured to be uniform.

In an embodiment, j is 1, which not only ensures the high glass transition temperature of the molecule, but also is beneficial to the thermal stability of the molecule, thereby further improving the service life and stability of the device; and avoiding the risk of thermal decomposition caused by high temperature which is required in the vapor deposition of a compound with an extremely high molecular weight, thereby avoiding unnecessary troubles during device fabrication.

In an embodiment, the compound includes any one of the following compounds represented by structures HB01-HB48:

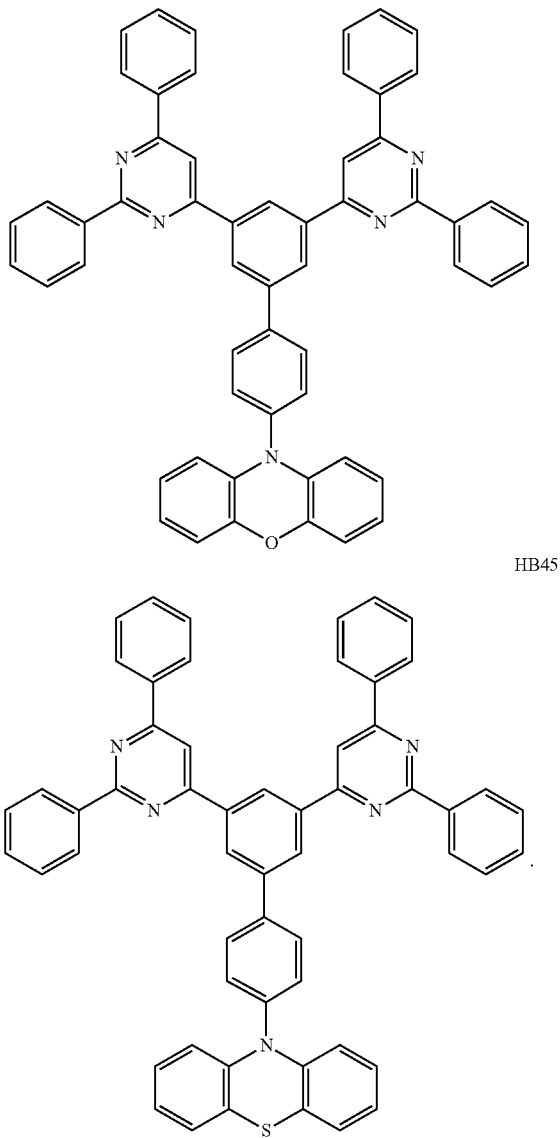

In a second aspect, the present disclosure provides an OLED display panel, which comprises a first electrode, a second electrode, and an organic thin film layer disposed between the first electrode and the second electrode; wherein the organic thin film layer comprises an electron transport layer; wherein the material of the electron transport layer comprises any one or a combination of at least two of the compounds as described in the first aspect.

The organic thin film layer further comprises an electron injection layer, wherein the electron injection layer comprises any one or a combination of at least two of the compounds as described.

In an embodiment, the organic thin film layer further comprises a light-emitting layer, wherein the main material of the light-emitting layer comprises any one or a combination of at least two of the compounds as described in the first aspect.

In an embodiment, the OLED display panel comprises any one or a combination of at least two of a group consisting of a hole transport layer, a hole injection layer, an electron blocking layer, and a hole blocking layer.

In the OLED display panel provided by the present disclosure, the material of the first electrode (the anode) may be selected from metals such as copper, gold, silver, iron, chromium, nickel, manganese, palladium, platinum, etc., and an alloy thereof. The material of the first electrode may also be selected from metal oxides such as indium oxide, zinc oxide, indium tin oxide (ITO), indium zinc oxide (IZO), etc.; the material of the first electrode may also be selected from conductive polymers such as polyaniline, polypyrrole, poly(3-methylthiophene), etc. In addition to the materials of the first electrode as listed above, the material of the first electrode may also be selected from materials that facilitate hole injection, including materials known to be suitable for use as the first electrode.

In the OLED display panel provided by the present disclosure, the material of the second electrode (the cathode) may be selected from metals such as aluminum, magnesium, silver, indium, tin, titanium, etc., and an alloy thereof. The material of the second electrode may also be selected from multi-layer metal materials such as LiF/Al, $LiO_2$/Al, $BaF_2$/Al, etc. In addition to the materials of the second electrode as listed above, the material of the second electrode may also be selected from materials that facilitate electron injection, including materials known to be suitable for use as the second electrode.

The substrate of the OLED display panel may be a rigid substrate, such as borosilicate glass, soda-lime (float) glass, high-refractive index glass, stainless steel, etc., or may be a flexible substrate, such as a polyimide (PI) plastic substrate, polyethylene terephthalate (PET) plastic substrate, polyethylene naphthalate (PEN) plastic substrate, polyether sulfone resin (PES) substrate, polycarbonate (PC) plastic substrate, an ultrathin flexible glass substrate, a metal foil substrate, etc.

In the OLED display panel provided by the present disclosure, the hole injection material, the hole transport material and the electron blocking material each is independently any one or a combination of at least two selected from a group consisting of N,N'-diphenyl-N,N'-(1-naphthyl)-1,1'-biphenyl-4,4'-diamine, 4,4',4"-tris(carbazol-9-yl)triphenylamine, 1,3-dicarbazol-9-ylbenzene, 4,4'-bis(9-carbazole)biphenyl, 3,3'-bis(N-carbazolyl)-1,1'-biphenyl, 2,3,6,7,10,11-hexacyano-1,4,5,8,9,12-hexaazabenzophenanthrene, 4,4'-cyclohexylbis[N,N-bis(4-methylphenyl)aniline, N,N'-diphenyl-N,N'-(1-naphthyl)-1,1'-biphenyl-4,4'-diamine, N,N'-di(naphthalen-2-yl)-N,N'-di(phenyl)biphenyl-4,4'-diamine, poly(3,4-ethylenedioxythiophene)-polystyrene sulfonic acid, polyvinyl carbazole, 9-phenyl-3,9-bicarbazole, and molybdenum trioxide.

In the OLED display panel provided by the present disclosure, the luminescent material includes a host material and a guest material. Wherein the host material is any one or more selected from a group consisting of 2,8-bis(diphenylphosphoryl)dibenzothiophene (PPT), 4,4'-bis(9-carbazole)biphenyl (CBP), 2,8-bis(diphenylphosphoryl)dibenzofuran (PPF), bis(4-(9H-carbazolyl-9-yl)phenyl) diphenylsilane (SiCz), bis(2-(diphenylphosphino)phenyl) ether oxide (DPEPO), 1,3-bis[3,5-di(pyridin-3-yl)phenyl] benzene (BMPYPHB), 4,6-bis(3,5-di(3-pyridine)phenyl)-2-methylpyrimidine (B3PYMPM), 9-(3-(9H-carbazolyl-9-yl) phenyl)-9H-carbazole-3-cyano (mCPCN), 9-phenyl-9-[4-(triphenylsilyl)phenyl]-9H-fluorene (TPSi-F), polyvinylcarbazole (PVK) and polyfluorene (PFO), or any one or a combination of at least two selected from a group consisting of the compounds as provided in the first aspect. The guest material is selected from a group consisting of fluorescent materials, phosphorescent materials, and thermally activated delayed fluorescent materials. The fluorescent material may be, for example, selected from a group consisting of BczVBi, coumarin-6, DCJTB, etc., and the phosphorescent material may be, for example, selected from an Ir complex, a Pt complex, a Cu complex, an Os complex, etc.

In the OLED display panel provided by the present disclosure, the hole blocking material is any one or a combination of at least two selected from a group consisting of 2,8-bis(diphenylphosphinyl)dibenzothiophene, TSPO1, TPBi, 2,8-bis(diphenylphosphoryl)dibenzofuran, bis(2-(diphenylphosphino)phenyl)ether oxide, lithium fluoride, 4,6-bis(3,5-di(3-pyridine)ylphenyl)-2-methylpyrimidine, 4,7-diphenyl-1,10-phenanthroline, 1,3,5-tris[(3-pyridyl)-3-phenyl]benzene, tris[2,4,6-trimethyl-3-(3-pyridyl)phenyl]borane, 1,3-bis(3,5-dipyridin-3-ylphenyl)benzene, 1,3-bis[3,5-di(pyridine-3-yl)phenyl]benzene, 2,4,6-tris(biphenyl-3-yl)-1,3,5-triazine, diphenylbis[4-(pyridin-3-yl)phenyl]silane, cesium carbonate, bis(2-methyl-8-hydroxyquinoline-N1,O8)-(1,1'-biphenyl-4-hydroxy)aluminum, 8-hydroxyquinoline-lithium, and tris(8-hydroxyquinoline) aluminum.

In an embodiment of the present disclosure, the OLED display panel is prepared by forming an anode (a first electrode) on a transparent or non-transparent smooth substrate, forming an organic thin layer on the anode, and forming a cathode (a second electrode) on the organic thin layer. The formation of the organic thin layer can be carried out by known film formation methods such as evaporation, sputtering, spin coating, dipping, ion plating and the like.

In a third aspect, the present disclosure provides an electronic device, which comprises the OLED display panel as described in the second aspect.

In an embodiment, the electronic device may be a mobile phone, a computer, a liquid crystal television, a smart watch, a smart car, a VR or an AR helmet, or the like.

The present disclosure provides exemplary methods of preparation several compounds according to Formula (1). In the subsequent preparation examples, the synthesis of compounds is exemplified.

Preparation Example 1

Preparation of Compound HB03

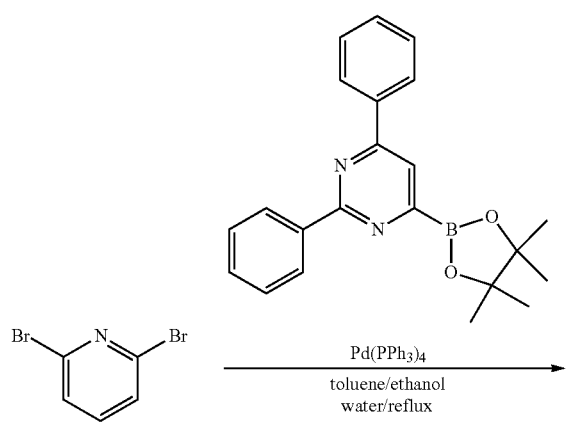

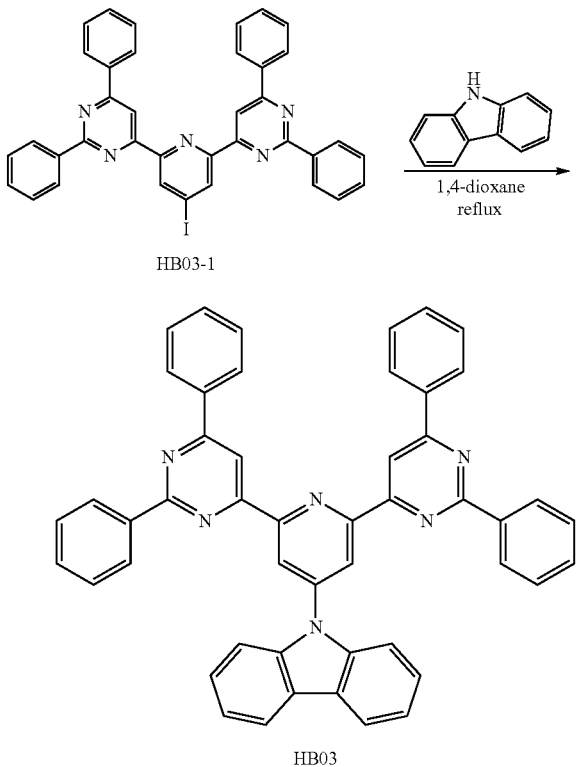

The preparation method was described as follows:

(1) Preparation of Compound HB03-1:

In a 250 mL round bottom flask, 2,6-dibromo-4-iodo-pyridine (10 mmol), 2,4-diphenyl-6-borate-pyrimidine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB03-1.

(2) Preparation of Compound HB03:

In a 250 mL round bottom flask, the intermediate product HB03-1, copper iodide (15 mmol), potassium t-butoxide (65 mmol), 1,2-diaminocyclohexane (12 mmol) and 9H-carbazole (25 mmol) were added to dry 1,4-dioxane (150 mL). The mixture was refluxed for 48 h under a nitrogen atmosphere. The resulting intermediate was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford an intermediate product HB03.

Elemental analysis results of Compound HB03 (Molecular Formula $C_{49}H_{32}N_6$): calculated: C, 83.50; H, 4.58; N, 11.92. found: C, 83.50; H, 4.59; N, 11.91. ESI-MS (m/z) (M+) obtained by liquid chromatography-mass spectrometry: calculated: 704.27. found: 704.82.

Preparation Example 2
Preparation of Compound HB11
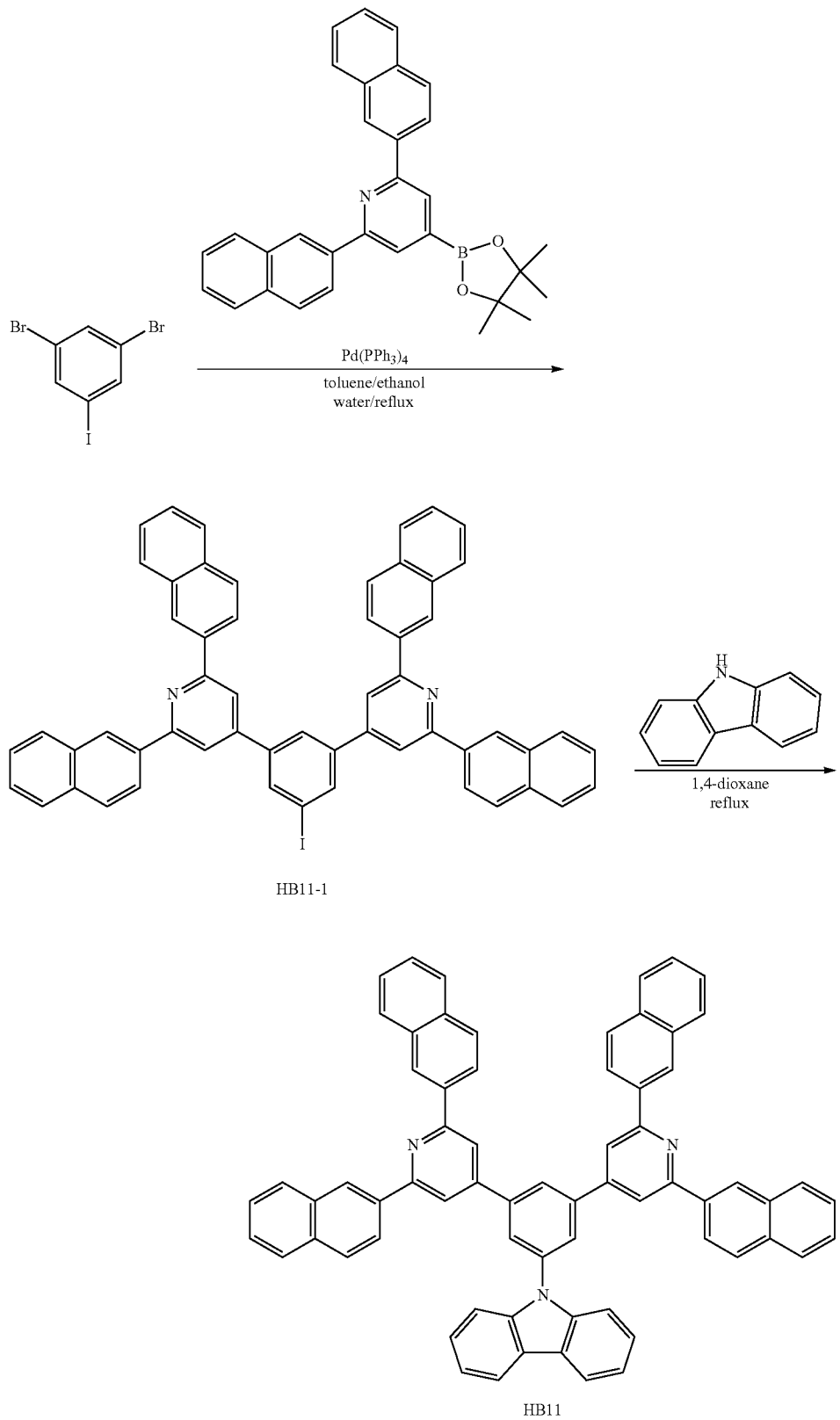

The preparation method was as follows:
(1) Preparation of Compound HB11-1:

In a 250 mL round bottom flask, 2,6-dibromo-4-iodobenzene (10 mmol), 2,6-dinaphthyl-4-borate-pyridine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB11-1.

(2) Preparation of Compound HB11:

In a 250 mL round bottom flask, the intermediate product HB11-1, copper iodide (15 mmol), potassium t-butoxide (65 mmol), 1,2-diaminocyclohexane (12 mmol) and 9H-carbazole (25 mmol) were added to dry 1,4-dioxane (150 mL). The mixture was refluxed for 48 h under a nitrogen atmosphere. The resulting intermediate was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford an intermediate product HB11.

Elemental analysis results of Compound HB11 (Molecular Formula $C_{68}H_{43}N_3$): calculated: C, 90.54; H, 4.80; N, 4.66. found: C, 90.55; H, 4.79; N, 4.66. ESI-MS (m/z)(M+) obtained by liquid chromatography-mass spectrometry: calculated: 901.35. found: 902.09.

Preparation Example 3

Preparation of Compound HB35

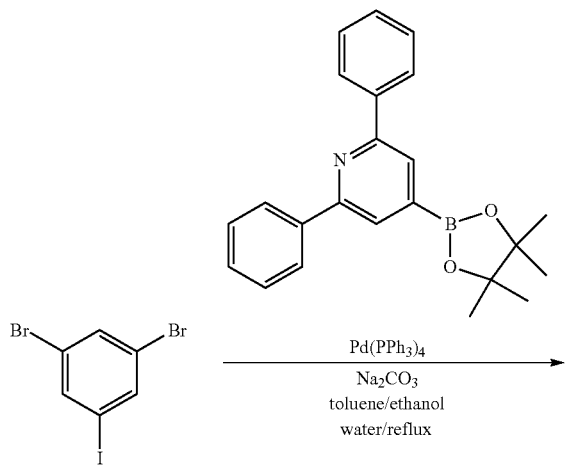

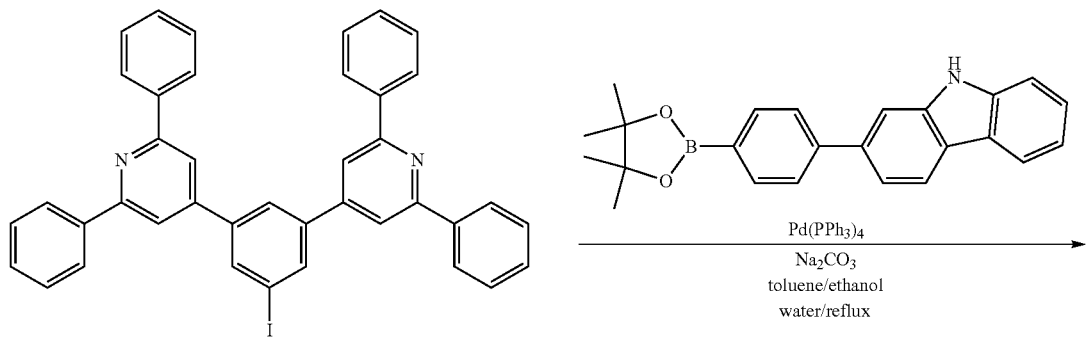

HB35-1

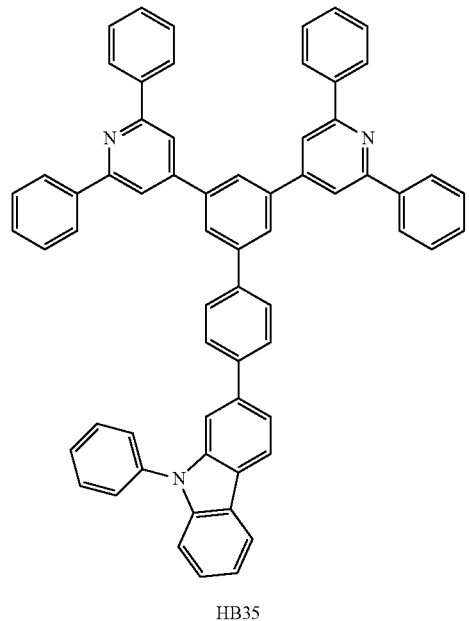

HB35

The preparation method was as follows:

(1) Preparation of Compound HB35-1:

In a 250 mL round bottom flask, 2,6-dibromo-4-iodo-benzene (10 mmol), 2,6-diphenyl-4-borate-pyridine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB35-1.

(2) Preparation of Compound HB35:

In a 250 mL round bottom flask, the intermediate product HB35-1 (10 mmol), 2-(4-borate)phenyl-carbazole (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB35.

Elemental analysis results of Compound HB35 (Molecular Formula $C_{64}H_{43}N_3$): calculated: C, 90.01; H, 5.07; N, 4.92. found: C, 90.02; H, 5.06; N, 4.92. ESI-MS (m/z)(M$^+$) obtained by liquid chromatography-mass spectrometry: calculated: 853.35. found: 854.05.

Preparation Example 4

Preparation of Compound HB44

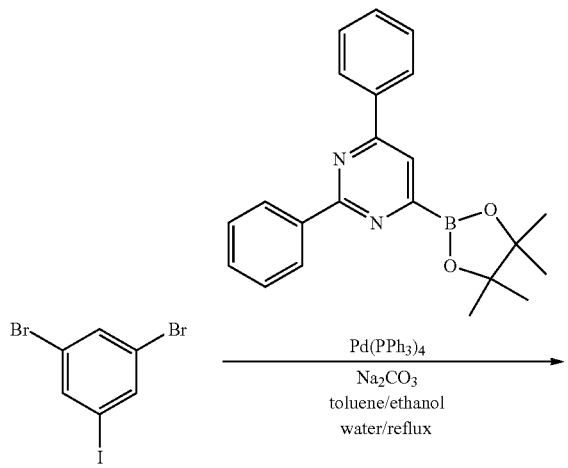

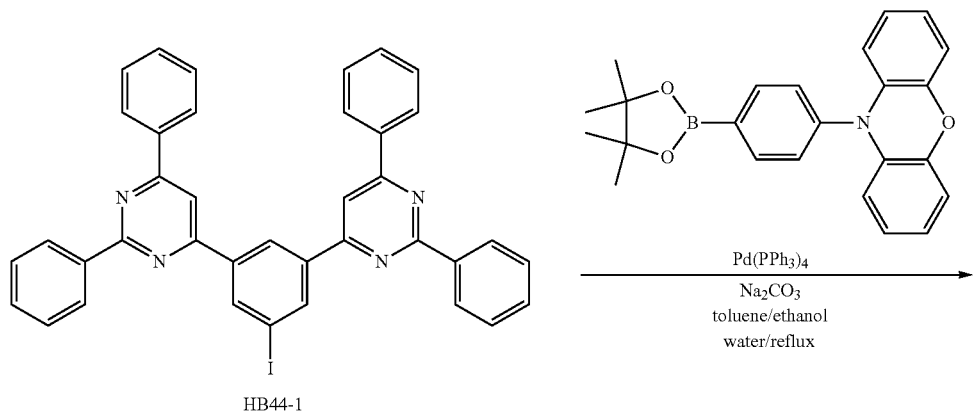

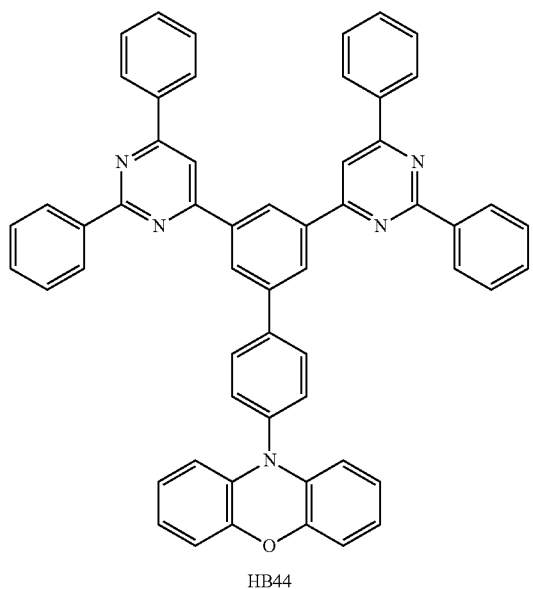

HB44

The preparation method was as follows:
(1) Preparation of Compound HB44-1:

In a 250 mL round bottom flask, 2,6-dibromo-4-iodo-benzene (10 mmol), 2,4-diphenyl-6-borate-pyrimidine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB44-1.

(2) Preparation of Compound HB44:

In a 250 mL round bottom flask, the intermediate product HB44-1 (10 mmol), 10-(4-borate)phenyl-phenoxazine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB44.

Elemental analysis results of Compound HB35 (Molecular Formula C$_{56}$H$_{37}$N$_5$O): calculated: C, 84.51; H, 4.69; N, 8.80; O, 2.01. found: C, 84.52; H, 4.68; N, 8.80; O, 2.01. ESI-MS (m/z)(M$^+$) obtained by liquid chromatography-mass spectrometry: calculated: 795.30. found: 795.93.

Preparation Example 5

Preparation of Compound HB31

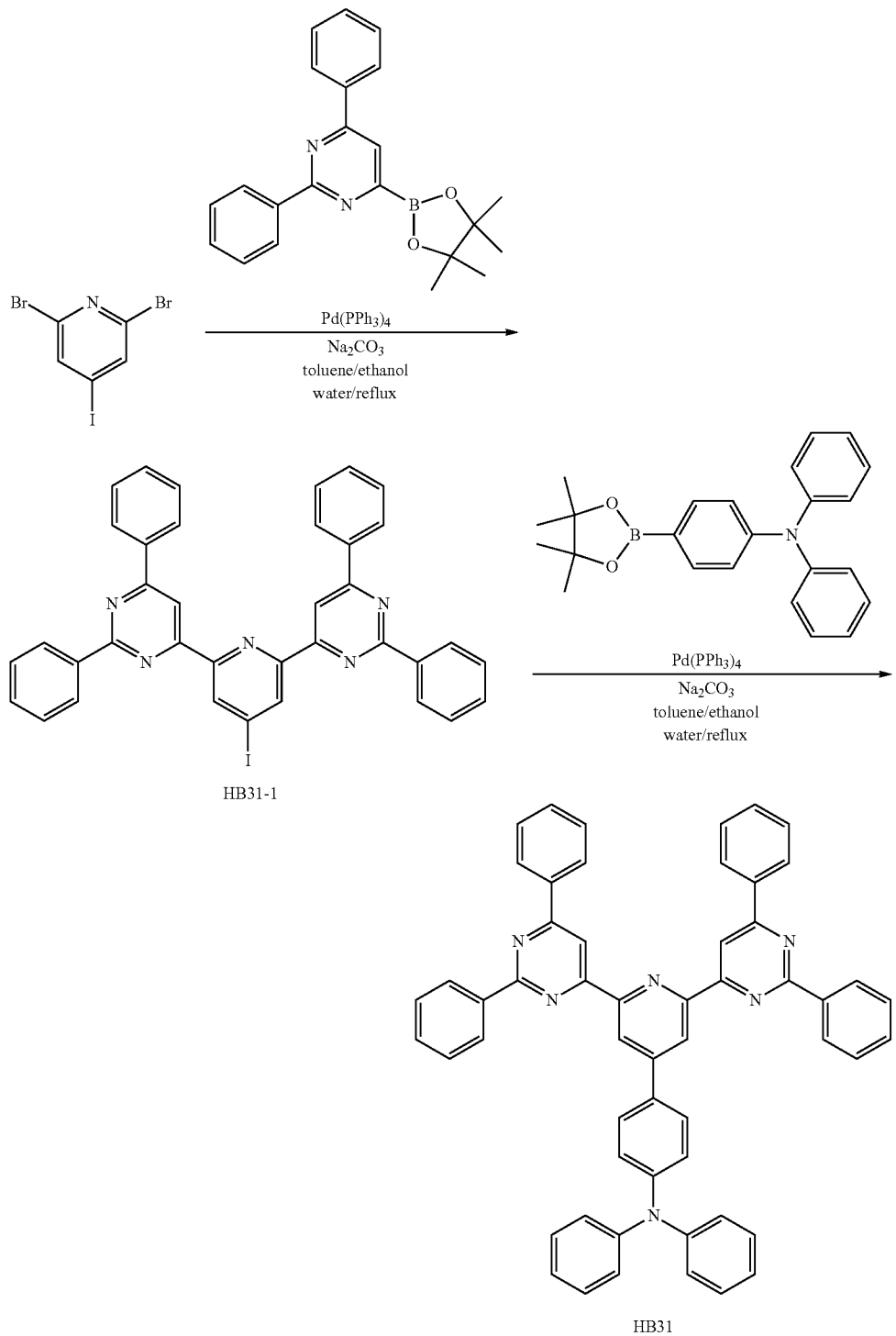

(1) Preparation of Compound HB31-1:

In a 250 mL round bottom flask, 2,6-dibromo-4-iodopyridine (10 mmol), 2,4-diphenyl-6-borate-pyrimidine (22 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB31-1.

(2) Preparation of Compound HB31:

In a 250 mL round bottom flask, the intermediate product HB31-1 (10 mmol), (4-boratephenyl)-diphenylamine (12 mmol) and Pd(PPh$_3$)$_4$ (0.3 mmol) were added to a mixture of toluene (30 mL)/ethanol (20 mL) and a solution of potassium carbonate (12 mmol) in water (10 mL). The mixture was refluxed for 12 h under a nitrogen atmosphere. The resulting mixture was cooled to room temperature, added to water, and then filtered through Celite pad. The filtrate was extracted with dichloromethane, washed with water, dried over anhydrous magnesium sulfate, filtered and evaporated. The crude product was then purified by silica gel column chromatography to afford a final product HB31.

Elemental analysis results of Compound HB31 (Molecular Formula C55H38N6): calculated: C, 84.37; H, 4.89; N, 10.73. found: C, 84.37; H, 4.88; N, 10.74. ESI-MS (m/z) (M$^+$) obtained by liquid chromatography-mass spectrometry: calculated: 782.32. found: 782.93.

The compounds prepared in Preparation Examples 1-5 were subject to simulation calculation.

The energy level difference between the singlet and triplet states of the organic materials was calculated with Guassian 09 software (Guassian Inc.). The detailed simulation method in calculating the energy level difference ΔEst was performed according to J. Chem. Theory Comput., 2013, DOI: 10.1021/ct400415r. The optimization of the molecular structure and the excitation were performed by using a TD-DFT method "B3LYP" and a basis set of "6-31 g(d)". Tg was measured by differential scanning calorimetry. Compounds prepared in Preparation Examples 1-8 cument6.0, EMBED ChemDraw.Document.6.0, EMBED ChemDraw.Document6 the results are shown in Table 1.

TABLE 1

| Example NO. | Compound NO. | HOMO (ev) | LUMO (ev) | $E_g$ (ev) | $E_T$ (ev) | $T_g$ (° C.) |
|---|---|---|---|---|---|---|
| Example 1 | HB03 | 5.83 | 2.68 | 3.15 | 2.89 | 128 |
| Example 2 | HB11 | 5.78 | 2.59 | 3.03 | 2.80 | 132 |
| Example 3 | HB35 | 5.76 | 2.59 | 3.17 | 2.91 | 129 |
| Example 4 | HB44 | 5.64 | 2.64 | 2.92 | 2.83 | 137 |
| Example 5 | HB31 | 5.70 | 2.60 | 2.90 | 2.85 | 135 |

It can be seen from Table 1 that all the compounds in the examples of the present disclosure had a triplet energy level of greater than 2.8 eV, and a glass transition temperatures of greater than about 127° C. Meanwhile, the materials of the examples of the present disclosure had a triplet energy level of greater than 2.8 eV and thus can be effectively utilized in blue light to prevent excitons from transporting backward, so that the excitons were confined in the light-emitting region, which was beneficial to broadening the light-emitting region and improving the luminous efficiency and service life of the device.

Hereinafter, the present disclosure will be explained in detail by the following examples in order to better understand the various aspects and advantages of the present disclosure. However, it should be understood that the following examples are non-limiting and merely used to illustrate certain embodiments of the present disclosure.

Example 1

As shown in FIG. 1, the present example provides an OLED display panel which comprises a substrate 1, an ITO anode 2, a hole injection layer 3, a first hole transport layer 4, a second hole transport layer 5, a light-emitting layer 6, a first electron transport layer 7, a second electron transport layer 8, an electron injection layer 9 and a cathode 10 (an aluminum electrode), wherein the thickness of the ITO anode 2 was 10 nm, the thickness of the hole injection layer 3 was 5 nm, the thickness of the first hole transport layer 4 was 50 nm, the thickness of the second hole transport layer 5 was 10 nm, the thickness of the light-emitting layer 6 was 20 nm, the thickness of the first electron transport layer 7 was 5 nm, the thickness of the second electron transport layer 8 was 20 nm, the thickness of the electron injection layer 9 was 1 nm, and the thickness of the aluminum electrode 10 was 15 nm, wherein the arrow in the figure indicates the direction of light.

The preparation steps of the OLED display panel were as follows:

1) A glass substrate 1 was cut into a size of 50 mm×50 mm×0.7 mm, sonicated in isopropanol and deionized water for 30 minutes, separately, and then exposed to ozone for about 10 minutes for cleaning. The obtained glass substrate with an ITO anode 2 was mounted on a vacuum deposition equipment;

2) A hole injection layer material HAT-CN having a thickness of 5 nm was deposited on the ITO anode layer 2 by vacuum evaporation at a vacuum degree of 2×10$^{-6}$ Pa and was used as a hole injection layer 3;

3) A first hole transport layer 2 material, N, N'-diphenyl-N, N'-(1-naphthyl)-1,1'-biphenyl-4,4'-diamine (α-NPD), having a thickness of 50 nm was deposited on the hole injection layer 3 by vacuum evaporation and was used as a first hole transport layer 4;

4) A second hole transport layer 5 material, 1,3-dicarbazol-9-ylbenzene (mCP), having a thickness of 10 nm was deposited on the first hole transport layer 4 by vacuum evaporation and was used as a second hole transport layer 5;

5) A light-emitting layer 6 was co-deposited on the second hole transport layer 5, wherein the light-emitting layer 6 had a thickness of 20 nm and comprised CBP as the host material and Ir(pyy)$_3$ as the guest material wherein the mass ratio of the compound CBP to Ir(ppy)$_3$ was 97:3;

6) A first electron transport layer 7 having a thickness of 5 nm was deposited on the light-emitting layer 6 by vacuum evaporation, wherein the material of the first electron transport layer 7 was HB03 as prepared in Preparation Example 1;

7) A second electron transport layer 8 having a thickness of 20 nm was deposited on the first electron transport layer 7 by vacuum evaporation, wherein the material of the second electron transport layer 8 was BPen;

8) An electron injection layer 9 having a thickness of 1 nm was deposited on the second electron transport layer 8 by vacuum evaporation, wherein the material of the electron injection layer 9 was LiF;

9) An aluminium electrode having a thickness of 15 nm was deposited on the electron injection layer 9 by vacuum evaporation and was used as a cathode 10.

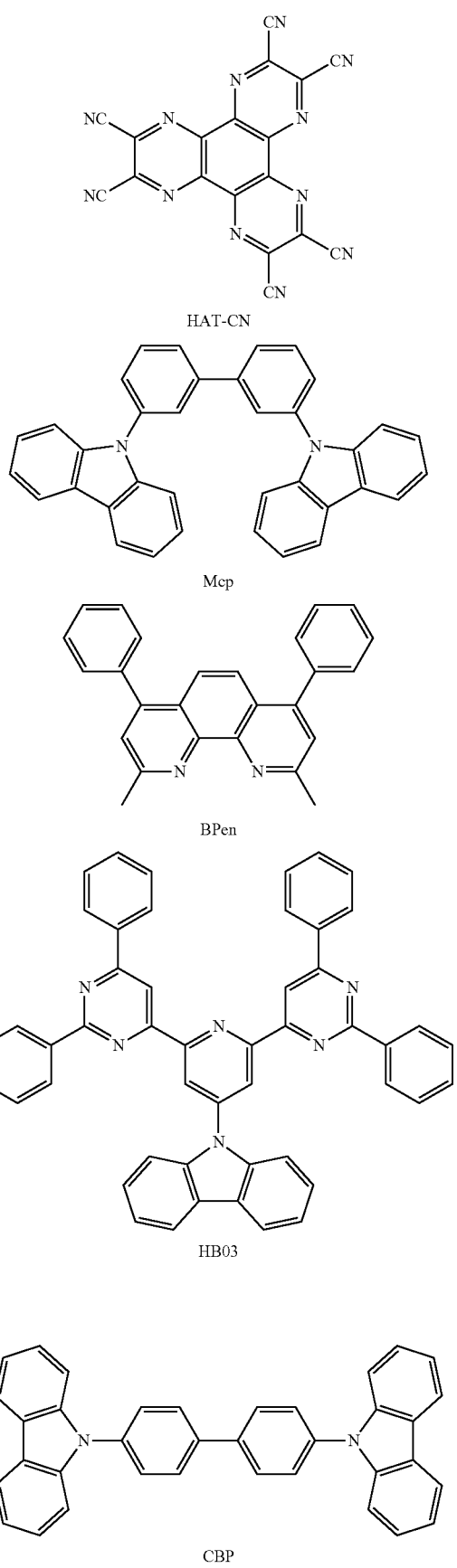
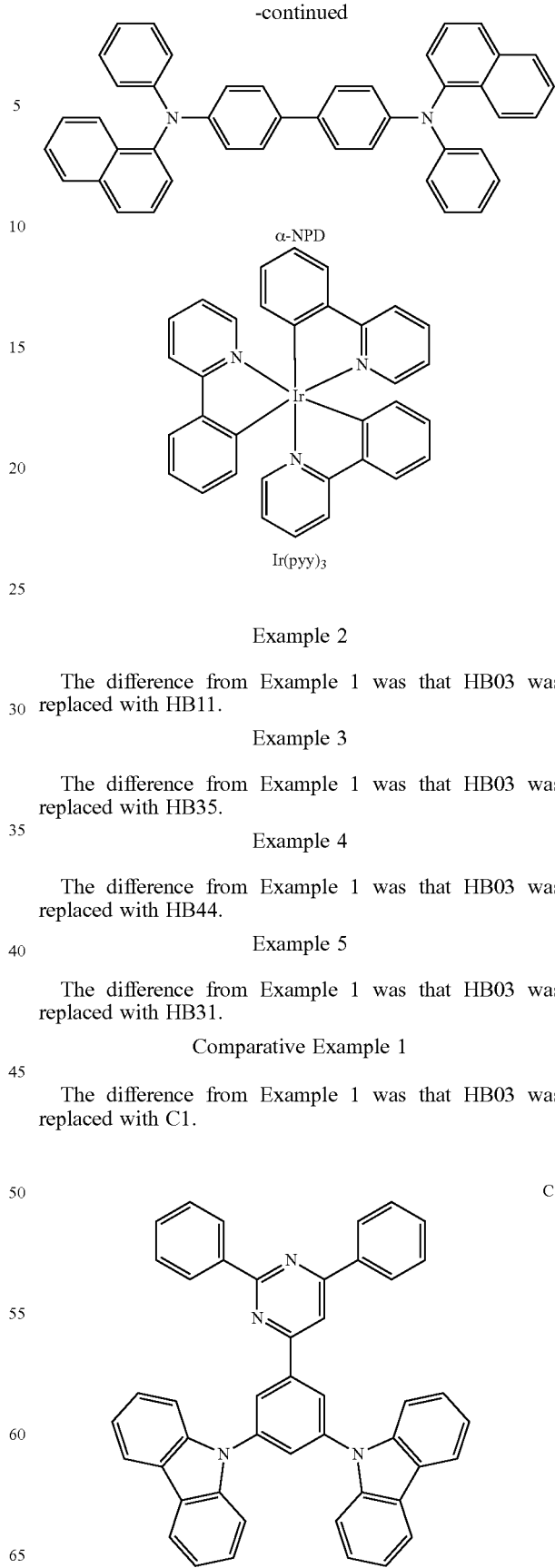
Example 2
The difference from Example 1 was that HB03 was replaced with HB11.
Example 3
The difference from Example 1 was that HB03 was replaced with HB35.
Example 4
The difference from Example 1 was that HB03 was replaced with HB44.
Example 5
The difference from Example 1 was that HB03 was replaced with HB31.
Comparative Example 1
The difference from Example 1 was that HB03 was replaced with C1.

Test of OLED Display Panel Performance:

OLED display panels were prepared by using compounds prepared in Preparation Examples 1-5 as shown in Table 1 and Compound C1 used in the comparative example as the material of an electron transport layer, respectively, and measured for efficiency and voltage with a Spectroscan PR 705 spectrometer and a Keithley 236 current-voltage source measure system at a current density of 10 mA/cm$^2$. The LT95 lifetime was measured as follows. The time in hours required for the brightness of the organic electroluminescent device to be decreased from 10000 cd/m$^2$ to 9500 cd/m$^2$ while keeping the current constant was measured. Results are shown in Table 2.

TABLE 2

| Example NO. | Compound NO. | Voltage (V) | Current efficiency (Cd/A) | Life time (LT95) |
|---|---|---|---|---|
| Example 1 | HB03 | 3.68 | 124.3 | 70 |
| Example 2 | HB11 | 3.70 | 126.1 | 72 |
| Example 3 | HB35 | 3.62 | 124.2 | 73 |
| Example 4 | HB44 | 3.69 | 125.8 | 72 |
| Example 5 | HB31 | 3.65 | 124.8 | 71 |
| Comparative Example 1 | C1 | 3.78 | 108.2 | 63 |

It can be seen from Table 2 that the OLED display panels provided by the present disclosure had a lower driving voltage, a higher luminous efficiency and a higher service life, wherein the driving voltage was less than 3.70 V, the luminous efficiency was greater than 120 Cd/A, and the service life was greater than 70 h. Compared with Comparative Example 1, the above performances of the display panels had been significantly improved, which was mainly due to the fact that the materials of the present disclosure had a shallow LUMO level, which was more matched with the energy level of the adjacent light-emitting layer; and a higher triplet energy level which could effectively prevent excitons from reflowing and holes from passing through the light-emitting layer.

Example 6

As shown in FIG. 1, the present example provides an OLED display panel which comprises a substrate 1, an ITO anode 2, a hole injection layer 3, a first hole transport layer 4, a second hole transport layer 5, a light-emitting layer 6, a first electron transport layer 7, a second electron transport layer 8, an electron injection layer 9 and a cathode 10 (an aluminum electrode), wherein the thickness of the ITO anode 2 was 10 nm, the thickness of the hole injection layer 3 was 5 nm, the thickness of the first hole transport layer 4 was 50 nm, the thickness of the second hole transport layer 5 was 10 nm, the thickness of the light-emitting layer 6 was 20 nm, the thickness of the first electron transport layer 7 was 5 nm, the thickness of the second electron transport layer 8 was 20 nm, the thickness of the electron injection layer 9 was 1 nm, and the thickness of the aluminum electrode 10 was 15 nm.

The preparation steps of the OLED display panel were as follows:

1) A glass substrate 1 was cut into a size of 50 mm×50 mm×0.7 mm, sonicated in isopropanol and deionized water for 30 minutes, separately, and then exposed to ozone for about 10 minutes for cleaning. The obtained glass substrate with an ITO anode 2 was mounted on a vacuum deposition equipment;

2) A hole injection layer material HAT-CN having a thickness of 5 nm was deposited on the ITO anode 2 by vacuum evaporation at a vacuum degree of 2×10$^{-6}$ Pa and was used as a hole injection layer 3;

3) A first hole transport layer 2 material, N, N'-diphenyl-N, N'-(1-naphthyl)-1,1'-biphenyl-4,4'-diamine (α-NPD), having a thickness of 50 nm was deposited on the hole injection layer 3 by vacuum evaporation and was used as a first hole transport layer 4;

4) A second hole transport layer 5 material, 1,3-dicarbazol-9-ylbenzene (mCP), having a thickness of 10 nm was deposited on the first hole transport layer 4 by vacuum evaporation and was used as a second hole transport layer 5;

5) A light-emitting layer 6 was co-deposited on the second hole transport layer 5, wherein the light-emitting layer 6 had a thickness of 20 nm and comprised HB03 prepared in Preparation Example 1 as the host material and FIrpic as the guest material wherein the mass ratio of Compound HB03 to FIrpic was 97:3;

6) A first electron transport layer 7 having a thickness of 5 nm was deposited on the light-emitting layer 6 by vacuum evaporation, wherein the material of the first electron transport layer 7 was BPen;

7) A second electron transport layer 8 having a thickness of 20 nm was deposited on the first electron transport layer 7 by vacuum evaporation, wherein the material of the second electron transport layer 8 was Alq3;

8) An electron injection layer 9 having a thickness of 1 nm was deposited on the second electron transport layer 8 by vacuum evaporation, wherein the material of the electron injection layer 9 was LiF;

9) An aluminium electrode having a thickness of 15 nm was deposited on the electron injection layer 9 by vacuum evaporation and was used as a cathode 10.

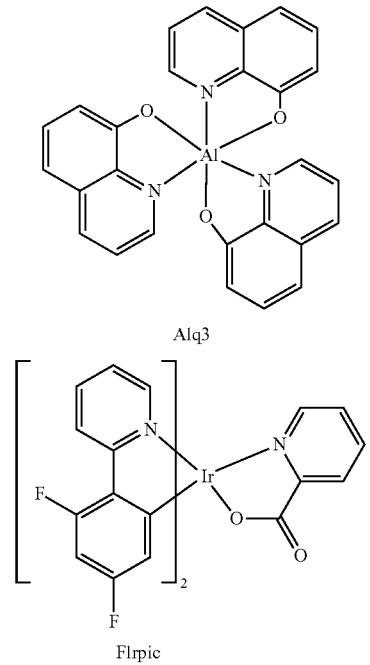

Alq3

FIrpic

Example 7

The difference from Example 6 was that HB03 was replaced with HB11.

Example 8

The difference from Example 6 was that HB03 was replaced with HB35.

Example 9

The difference from Example 6 was that HB03 was replaced with HB44.

Example 10

The difference from Example 6 was that HB03 was replaced with HB31.

Comparative Example 2

The difference from Example 6 was that HB03 was replaced with C1.

OLED display panels were prepared by using compounds prepared in Preparation Examples 1-5 and Compound C1 used in the comparative example as the host material of the light-emitting layer, respectively, and detected for performance. The specific detection method was the same as described above, and the detection results were shown in Table 3:

TABLE 3

| Example No. | Compound No. | Voltage (V) | Current efficiency (Cd/A) | Life time (LT95) |
|---|---|---|---|---|
| Example 6 | HB03 | 3.69 | 70.6 | 70 |
| Example 7 | HB11 | 3.70 | 71.5 | 71 |
| Example 8 | HB35 | 3.62 | 70.2 | 75 |
| Example 9 | HB44 | 3.69 | 71.8 | 72 |
| Example 10 | HB31 | 3.67 | 70.9 | 74 |
| Comparative Example 2 | C1 | 3.78 | 64.8 | 63 |

It can be seen from Table 3 that, as compared with Comparative Example 2, the OLED display panels provided by the present disclosure had a smaller operating voltage of <3.70 V, which was improved by about 3%; a higher current efficiency of greater than 70 cd/A, which was improved by about 10%; and a longer device lifetime of >70 h, which was improved by more than 11%. The above performances of the display panels had been significantly improved, which was mainly due to the high triplet energy levels of the materials of the present disclosure. The high triplet energy level could effectively transfer energy from the host material to the guest luminescent material, prevent excitons from transporting backward, broaden the light-emitting region, effectively improve the utilization of excitons and improve the photoluminescence efficiency.

Figure 2:
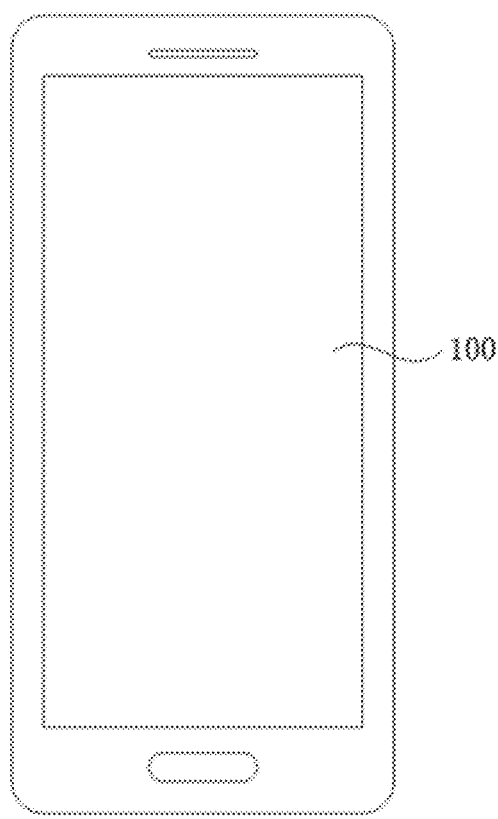
FIG. 2 shows a schematic view of an electronic device provided in accordance of the embodiment.

Yet another aspect of an embodiment of the present disclosure provides an electronic device, which comprises the OLED display panel as described above. The electronic device may be any electronic device having a display function such as a touch display screen, a mobile phone, a tablet computer, a notebook computer, an electronic paper book, a television, a VR or AR helmet or a smart watch. FIG. 2 shows a schematic view of an electronic device provided in an example of the present disclosure, wherein 1 represents a mobile phone display screen.

The applicant states that detailed equipment and process of the present application are demonstrated in the present application through the above embodiments, however, the present application is not limited to the above detailed equipment and process, that is, it does not mean that the present application must rely on the above detailed equipment and process to implement. It should be apparent to those skilled in the art that, for any improvement of the present application, the equivalent replacement of the raw materials of the present application, the addition of auxiliary components, and the selection of specific modes, etc., will all fall within the protection scope and the disclosure scope of the present application.

What is claimed is:

1. A compound, comprising a structure having Formula (I):

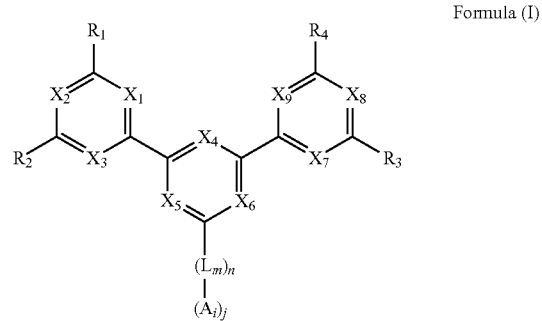

Formula (I)

wherein $R_1$, $R_2$, $R_3$ and $R_4$ each is independently any one selected from a group consisting of a substituted or unsubstituted C6-C40 aromatic ring and a substituted or unsubstituted C5-C40 heteroaromatic ring;

wherein $X_1$, $X_2$, $X_3$, $X_4$, $X_5$, $X_6$, $X_7$, $X_8$ and $X_9$ each is independently any one selected from a carbon atom or a nitrogen atom, and at least one of $X_1$, $X_2$, $X_3$, $X_4$, $X_5$, $X_6$, $X_7$, $X_8$ and $X_9$ is a nitrogen atom;

wherein $L_m$ is each independently any one selected from a group consisting of

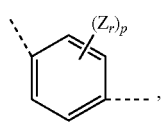

2-1

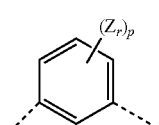

2-2

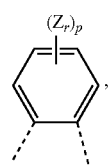

2-3

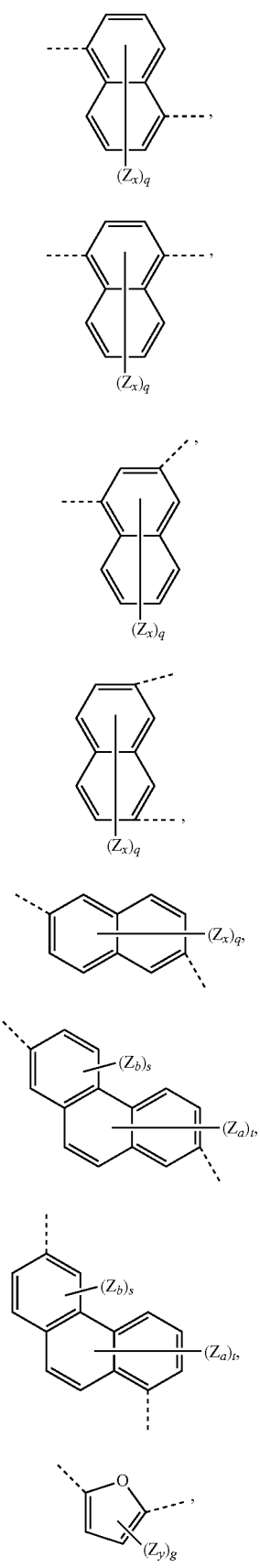

wherein $Z_r$, $Z_x$, $Z_a$, $Z_b$, $Z_y$, $Z_u$, $Z_o$ and $Z_v$ each is independently selected from a group consisting of a hydrogen atom, a substituted or unsubstituted C6-C30 aryl, a substituted or unsubstituted C6-C30 heteroaryl, a substituted or unsubstituted C6-C30 fused aryl, a substituted or unsubstituted C6-C30 fused heteroaryl, a substituted or unsubstituted C1-C16 alkylene, and a substituted or unsubstituted C1-C16 alkyleneoxy;

wherein p is an integer from 0 to 4, and r is an integer from 1 to p;

wherein q is an integer from 0 to 6, and x is an integer from 1 to q;

wherein s and t each is independently selected from an integer from 0 to 3, a is an integer from 1 to t, and b is an integer from 1 to s;

wherein g is an integer from 0 to 2, and y is an integer from 1 to g;

wherein c is an integer from 0 to 5, and u is an integer from 1 to c;

wherein d is an integer from 0 to 3, and o is an integer from 1 to d;

wherein e is an integer from 0 to 2, and v is an integer from 1 to e;

wherein a substituent is any one of a group consisting of a C1-C10 alkyl or cycloalkyl, a C2-C10 alkenyl, a C1-C6 alkoxy or thioalkoxy, a C6-C30 monocyclic aromatic hydrocarbon or fused aromatic hydrocarbon group, and a C3 to C30 monocyclic heteroaromatic hydrocarbon or fused heteroaromatic hydrocarbon group; and wherein a dotted line indicates an attachment site;

wherein n is 1, and m is 1;

wherein $A_i$ is each independently any one selected from a group consisting of

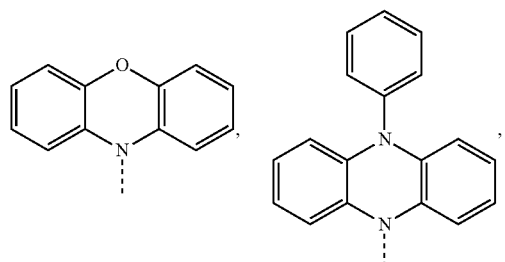

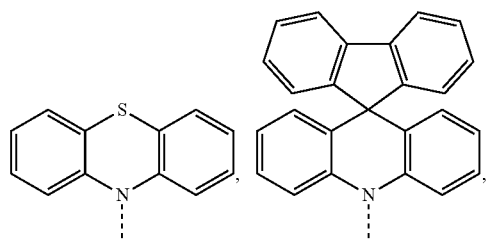

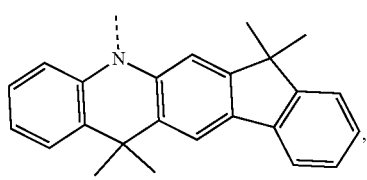

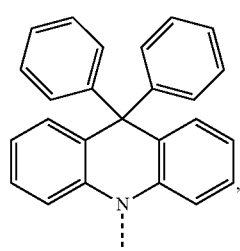

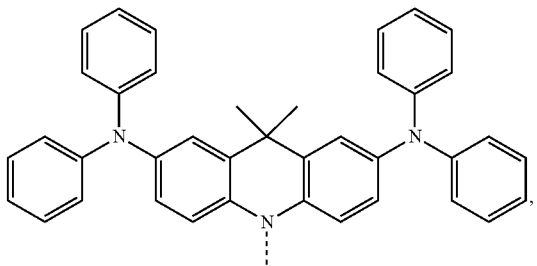

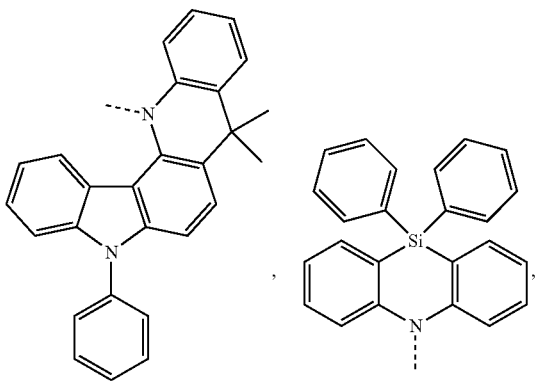

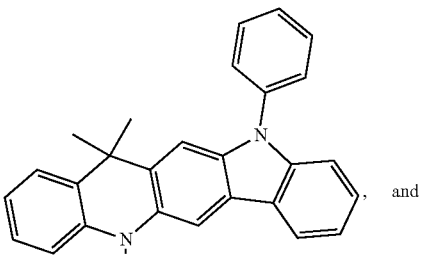

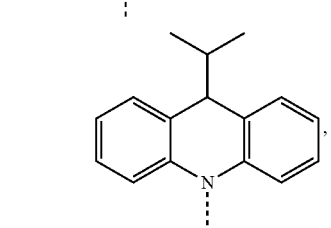

wherein a dotted line indicates an attachment site; and wherein j is an integer from 1 to 3.

2. The compound according to claim 1, wherein at least one of X1, X2, X3, X7, X8 and X9 is a nitrogen atom.

3. The compound according to claim 1, wherein two to six of X1, X2, X3, X4, X5, X6, X7, X8 and X9 are nitrogen atoms.

4. The compound according to claim 1, wherein Lm is each independently any one selected from a group consisting of

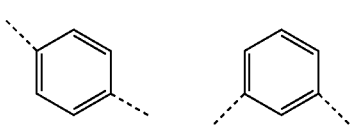

-continued

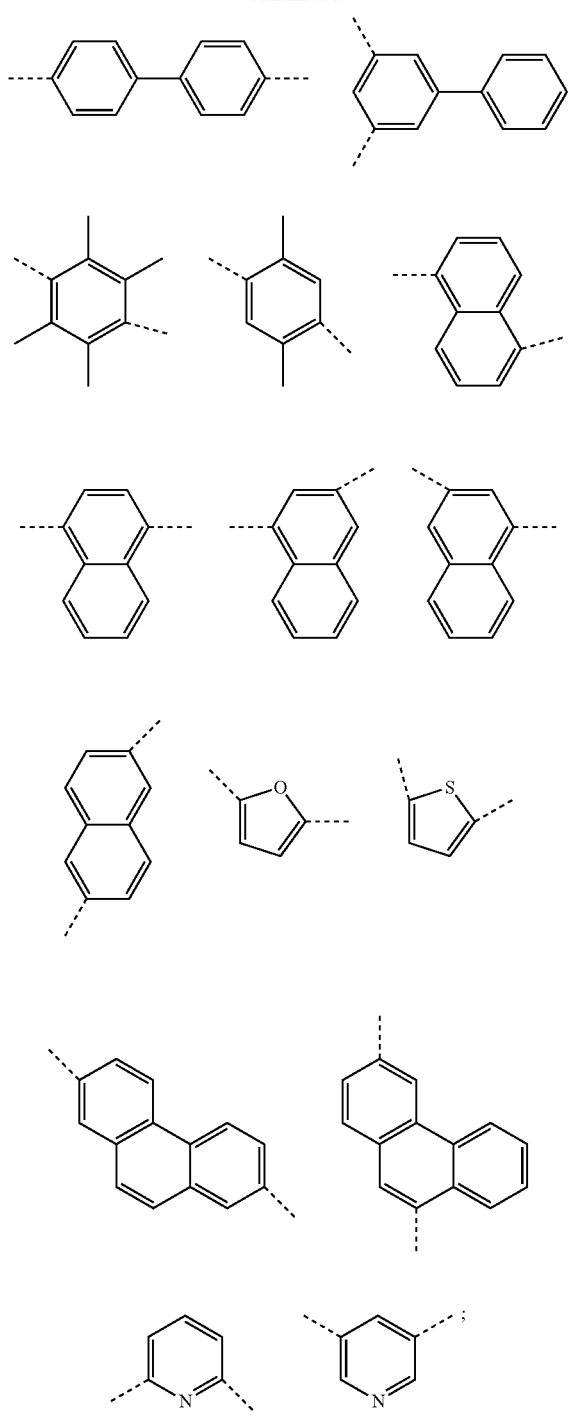

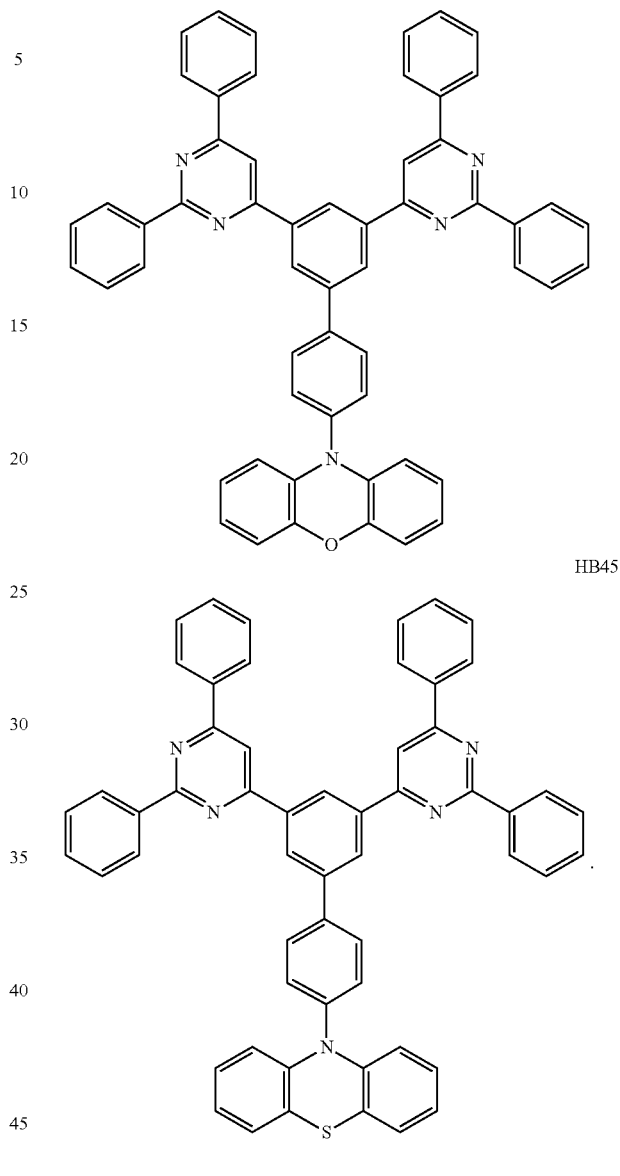

wherein a dotted line indicates an attachment site.

5. The compound according to claim 1, wherein R1 and R4 are the same, and R2 and R3 are the same.

6. The compound according to claim 1, wherein j is 1.

7. The compound according to claim 1, wherein the compound includes any one of the following compounds represented by structures HB44-HB45:

8. An OLED display panel comprising an organic thin film layer having one or more compound materials of Formula (I) of claim 1, the OLED display panel further comprises a first and a second electrodes, wherein the organic thin film layer is disposed between the first electrode and the second electrode and wherein the organic thin film layer comprises an electron transport layer.

9. The OLED display panel according to claim 8, wherein the organic thin film layer further comprises an electron injection layer, wherein a material of the electron injection layer comprises said one or more compounds in Formula (I).

10. The OLED display panel according to claim 8, wherein the organic thin film layer further comprises a light-emitting layer, wherein the light-emitting layer includes said one or more compounds in Formula (I).

11. An electronic device comprising the OLED display panel according to claim 8.

* * * * *